(12) United States Patent
Inbar

(10) Patent No.: US 8,920,318 B2
(45) Date of Patent: Dec. 30, 2014

(54) APPARATUS, METHOD AND COMPUTER READABLE CODE FOR FORECASTING THE ONSET OF POTENTIALLY LIFE-THREATENING DISEASE

(75) Inventor: Michael Inbar, Rehovot (IL)

(73) Assignee: Itegralis, Tel Aviv (IL)

( * ) Notice: Subject to any disclaimer, the term of this patent is extended or adjusted under 35 U.S.C. 154(b) by 1990 days.

(21) Appl. No.: 11/995,107

(22) PCT Filed: Jun. 12, 2006

(86) PCT No.: PCT/IL2006/000681
§ 371 (c)(1),
(2), (4) Date: Jul. 7, 2008

(87) PCT Pub. No.: WO2007/010521
PCT Pub. Date: Jan. 25, 2007

(65) Prior Publication Data
US 2009/0163776 A1    Jun. 25, 2009

Related U.S. Application Data

(60) Provisional application No. 60/699,996, filed on Jul. 18, 2005.

(51) Int. Cl.
| | | |
|---|---|---|
| *A61B 5/00* | (2006.01) | |
| *G06Q 10/00* | (2012.01) | |
| *G06F 19/00* | (2011.01) | |
| *A61B 5/0205* | (2006.01) | |
| *A61B 5/024* | (2006.01) | |
| *A61B 5/087* | (2006.01) | |

(52) U.S. Cl.
CPC ............ *G06F 19/3443* (2013.01); *A61B 5/412* (2013.01); *A61B 5/02055* (2013.01); *A61B 5/02411* (2013.01); *A61B 5/0008* (2013.01); *A61B 5/087* (2013.01); *A61B 5/024* (2013.01)
USPC .............................................. 600/301; 705/2

(58) Field of Classification Search
CPC ............... A61B 5/412; A61B 5/02055; A61B 5/02411; A61B 5/0008; A61B 5/087; A61B 5/024; A61B 5/4818; G06F 19/3443; G06F 19/345; G06F 19/322; G06F 19/3437; G06K 9/0053
USPC ......................................................... 600/301
See application file for complete search history.

(56) References Cited

U.S. PATENT DOCUMENTS 5,105,354 A * 4/1992 Nishimura .................... 600/484
6,216,032 B1 * 4/2001 Griffin et al. ................. 600/515
(Continued)

FOREIGN PATENT DOCUMENTS

WO    WO03/082073    3/2003

*Primary Examiner* — William Thomson
*Assistant Examiner* — Shirley Jian
(74) *Attorney, Agent, or Firm* — Mark M. Friedman

(57) ABSTRACT

Methods, systems and computer-readable code for generating a forecast of a life-threatening condition, for example sepsis, in a subject, for example an infant, are disclosed. According to some embodiments, the forecast is generated in accordance with measurement values for a plurality of different vital sign parameters. In exemplary embodiments, vital sign parameters from a plurality of physiological systems are used to generate the forecast of the life-threatening condition. In exemplary embodiments, at least one vital sign parameter is other than a cardiac parameter. Non-limiting exemplary vital sign parameters may include one or more of a heart rate parameter, a respiration rate parameter, a bradycardia parameter, a desaturation parameter, a temperature parameter (for example, body temperature) and a body mass parameter.

43 Claims, 11 Drawing Sheets

(56) References Cited

U.S. PATENT DOCUMENTS

| | | | |
|---|---|---|---|
| 6,330,469 B1 * | 12/2001 | Griffin et al. | 600/515 |
| 2003/0000522 A1 * | 1/2003 | Lynn et al. | 128/200.24 |
| 2003/0101076 A1 * | 5/2003 | Zaleski | 705/2 |
| 2003/0158466 A1 * | 8/2003 | Lynn et al. | 600/300 |
| 2006/0155207 A1 * | 7/2006 | Lynn et al. | 600/538 |
| 2006/0161071 A1 * | 7/2006 | Lynn et al. | 600/538 |
| 2006/0189880 A1 * | 8/2006 | Lynn et al. | 600/538 |
| 2008/0214903 A1 * | 9/2008 | Orbach | 600/301 |

* cited by examiner

APPARATUS, METHOD AND COMPUTER READABLE CODE FOR FORECASTING THE ONSET OF POTENTIALLY LIFE-THREATENING DISEASE

FIELD OF THE INVENTION

The present invention relates to apparatus, a method and computer readable code for forecasting the onset of potentially catastrophic diseases, including but not limited to sepsis, in patients, including but not limited to premature infants.

BACKGROUND

Introduction

Late-onset sepsis is an important problem in many infants, and particularly in premature infants as well as very low birthweight (VLBW) infants. Sepsis (one episode or more) can be detected in 25-40% of all hospitalized VLBW world wide. Sepsis may increase, dramatically, both mortality relates as well as length of hospitalization. This problem was lately summarized by the US National Institute of Child Health and Human Development as follows: "Successful strategies to decrease sepsis in preterm infants should decrease mortality, shorten hospital stay and reduce costs." Thus, there is an ongoing need for apparatus and methods for early detection of potentially catastrophic diseases (for example, sepsis) in infants (for example, premature infants and/or very low birthweight infants. Furthermore, it is noted that sepsis affects both infants as well as older patients.

Forecasting of Sepsis

Sepsis is a medical condition in which microorganisms such as bacteria invade the body causing a serious infection. Large and increasing numbers of microorganisms overwhelm the body's defense systems and actively multiply in the bloodstream. Sepsis is associated with a large stress on the body, such as trauma. There is an ongoing need for methods and apparatus for early detection of sepsis.

WO 03/082073 discloses a method and device for continuous monitoring of patients to detect the potential onset of sepsis. The device is configured to process measurement values for a plurality of vital signs and to generate an alarm signal indicative of the onset of sepsis. Each vital sign is associated with more one or more threshold values. For example, the "temperature" vital sign is associated with two threshold values—a high alarm limit of 38.3 degrees Celsius and a low alarm limit of 35.5 degrees Celsius. If the temperature exceeds the first threshold value (i.e. 38.3 degrees) or if the temperature is less than the second threshold value (i.e. 35.5 degrees), a conditional warning signal is asserted. The heartbeat threshold value is associated with a single threshold value —90 beats per minute. If the heartbeat rate exceeds this threshold value, a conditional warning signal is asserted.

If a certain pre-determined number of conditional warning signals are asserted concurrently (for example, at two out of four) an alarm signal, indicative of the onset of the condition, is generated.

Although the alarm signal is determined in accordance with a plurality of vital sign parameters, each vital sign is treated "separately" and the threshold values for a given vital sign (i.e. for which a conditional warning is asserted for a given vital sign) are independent of the measured values for another vital sign. For example, the threshold values for temperature are 35.5 degrees Celsius and 38.3 degrees Celsius, irrespective of the measured heartbeat or respiration rate. The threshold value for heartbeat is 90 beats per minute, irrespective of the measured values for respiration rate or temperature.

This is graphically illustrated in FIG. 1, which shows the "parameter space" for two vital sign parameters—heart rate (Y axis) and body temperature (X axis). As shown in FIG. 1, an alarm is asserted when the R1 or R3 of parameter space are occupied (i.e. measured values of body temperature and heartbeat produce a point in parameter space located in R1 or R3). It is noted that the boundary between the "alarm" boundary space and the "no alarm boundary space" is delineated by segments S1, S2, S3 and S4 which are each either parallel or perpendicular to each coordinate access of the parameter space.

Finally, it is noted that there is no disclosure or suggestion in WO 03/082073 of using the method of WO 03/082073 to monitor the potential onset of sepsis in infants, and in particular, premature infants and/or very low birthweight infants.

Forecasting of Potentially Catastrophic Diseases in Infants

U.S. Pat. No. 6,330,469 discloses a method and apparatus for the early detection of potentially catastrophic infectious illness in premature infants. The method comprises monitoring heart rate variability in the premature newborn infant and identifying at least one characteristic abnormality in the heart rate variability that is associated with the illness. There is ongoing an medical ongoing need for apparatus and methods for early detection of potentially catastrophic diseases (for example, systemic illness such as sepsis) in infants, for example, premature infants and/or very low birthweight infants. Such apparatus and methods could, for example, obviate the need to unnecessarily administer antibiotics (or to administer antibiotics for a longer period of time than is necessary), and could allow doctors to discharge infants from an NICU (neonatal intensive care unit) at an earlier time.

SUMMARY

Some or all of the aforementioned needs, and other needs, may be satisfied by several aspects of the present invention.

It is now disclosed for the first time a method of forecasting a life-threatening condition comprising: a) providing measurement values of a plurality of different vital sign parameters of an infant including a temperature parameter, a desaturation parameter, a heart rate parameter, a bradycardia parameter, and a respiration rate parameter; and b) generating a forecast of the life-threatening condition in the infant from said values, wherein said forecast is determined at least in part by said measurement values for each said vital sign parameter.

According to some embodiments, at least one said vital sign parameter is a body mass parameter (i.e. indicative of a body mass of the patient/infant).

It is now disclosed for the first time a method of forecasting a life-threatening condition comprising: a) providing measurement values of a plurality of different vital sign parameters of an infant; and b) generating a forecast of the life-threatening condition in the infant from said values, wherein said forecast is determined at least in part by said measurement values for each said vital sign parameter.

According to some embodiments, said generated forecast is indicative of a likelihood of an onset of the life-threatening condition. According to some embodiments, said generated forecast is indicative of a forecasted severity of the life-threatening condition.

In exemplary embodiments, vital sign parameters from a plurality of physiological systems are used to generate the forecast of the life-threatening condition.

Thus, according to some embodiments, a first said physiological parameter and a second said physiological parameter are associated with different respective physiological systems.

According to some embodiments, said generating of said forecast includes computing an arithmetic function (for example, computing a number indicative of a sum, different, product or quotient) of a first number derived from (i.e. indicative of) a measured value of a first said vital sign parameter and a second number from a measured value of a second said vital sign parameter that is different from said first vital sign parameter.

According to some embodiments, the method further comprises (c) generating an alarm signal in accordance with said forecast.

According to some embodiments, said generating includes generating a forecast for the onset of late-onset infant sepsis.

According to some embodiments, said infant is a pre-mature infant.

According to some embodiments, said infant is a very low birth weight infant.

According to some embodiments, said generated forecast is determined at least in part by a relation between a measured value of a first said vital sign parameter and at least one threshold value associated with said first vital sign, and at least one said threshold value for said first vital sign depends at least in part on a said measured value of a second vital sign different from said first vital sign.

According to some embodiments, at least one of said first vital sign parameter and said second vital sign parameter is other than a cardiac vital sign parameter.

According to some embodiments, one of said first vital sign parameter and said second vital sign parameter is a cardiac vital sign parameter and the other of said first vital sign parameter and said second vital sign parameter is other than a cardiac vital sign parameter.

According to some embodiments, said forecast is determined at least in part by a location in a parameter space having a boundary having a tangent that, at least one location, is oblique to a coordinate access of said parameter space.

According to some embodiments, said generated forecast is determined at least in part by a location in parameter space having a boundary, and at least one said vital sign parameter has at least three threshold values one said boundary;

According to some embodiments, values for at least one said vital sign parameter are collected for a plurality of times, and said forecast is determined at least in part by said values for said plurality of times.

According to some embodiments, at least one said vital sign parameter is other than a cardiac parameter.

According to some embodiments, at least one said vital sign parameter is indicative of a state of the skin (for example, a desaturation parameter).

According to some embodiments, one said physiological parameter is an age parameter (for example, a parameter indicative of a birth age or a gestational age of an infant).

According to some embodiments, at least one said vital sign parameter is a respiratory parameter (for example respiration rate, or a parameter indicative of an apnea condition).

According to some embodiments, at least one said vital sign parameter is a temperature parameter (e.g. a parameter indicative of a temperature of the subject/infant at any location in or on the infant's body).

According to some embodiments, at least one said vital sign parameter is a desaturation parameter.

According to some embodiments, at least one said vital sign parameter is a metabolic parameter (a parameter indicative of body metabolism, for example, a temperature)

According to some embodiments, at least one said vital sign parameter is indicative of a rate of gas exchange (for example, desaturation).

According to some embodiments, at least one said vital sign parameter is indicative of a skin condition (for example, desaturation).

According to some embodiments, at least one said vital sign parameter is indicative of a concentration of a substance in a biological fluid (for example, desaturation which is indicative of a concentration of complexed hemoglobin in blood)

According to some embodiments, at least one said vital sign parameter is indicative of a increase or decrease in tissue mass (for example, body mass).

According to some embodiments, at least one said vital sign parameter is indicative of a cell replication (for example, body mass).

According to some embodiments, at least one said vital sign parameter is a parameter indicative of an apnea condition (i.e. absence and/or presence and/or severity).

According to some embodiments, at least one said vital sign parameter is a respiration parameter (for example respiration rate, a statistical moment of respiration—for example a variance in the respiration rate, a frequency of occurrence of apnea events, etc).

According to some embodiments, at least one said vital sign parameter is a blood pressure parameter.

According to some embodiments, at least one said vital sign parameter is a digestion parameter (i.e. indicative of the contents of substances in the GI tract).

According to some embodiments, at least one said vital sign parameter is indicative of a homeostasis relationship between the patient and the external environment (for example, temperature, desaturation and/or respiration).

According to some embodiments, at least one said vital sign parameter is a cardiac parameter (for example, heart rate or frequency of bradycardia events).

According to some embodiments, values for at least one said vital sign parameter are normalized by at least an age parameter and a body mass parameter.

According to some embodiments, one said normalized vital sign parameter is a temperature parameter.

According to some embodiments, said generating of said forecast includes normalizing each of at least a sub-plurality of said plurality of said vital sign parameters in accordance with a respective normalization function that is different for each said vital sign parameter of said sub-plurality.

In exemplary embodiments, the technique involves: normalizing each physiological parameter separately, and then generating the forecast in accordance with a parameter computed by combining the normalized physiological parameters.

According to some embodiments, said generating of said forecast includes normalizing values of vital sign parameters, and a temperature parameter and a cardiac parameter are normalized using different functions.

According to some embodiments, said generating of said forecast includes normalizing a first said vital sign parameter in accordance with a past behavior of a set of vital sign parameters.

According to some embodiments, said set of vital sign parameters includes a vital sign parameter other than said first vital sign parameter.

It is noted that typically some parameters are obtained from electronic monitors which continuously monitor the subject/infant. Other parameters may be obtained typically less frequently. The generated forecast may thus be computed using some parameters with values at more frequent intervals, and other parameters with values at less frequent intervals.

According to some embodiments, for each said vital sign parameter, (i) said measured values are collected for a respective plurality of points in time; (ii) said forecast is generated in accordance with said measured values for said respective plurality of points in time; (iii) a ratio between an average time frequency for a first said physiological parameter to an average time frequency for a second sad physiological parameter is at least 2 (i.e. at least one parameter has values taken at least twice as often as another parameter).

In some embodiments, the ratio is at least 5, or at least 10.

According to some embodiments, the method further comprises effecting at least one of a course of treatment (for example, administering antibiotics, modifying a dosage, or stopping to administer antibiotics) and a diagnostic procedure in accordance with said generated forecast.

It is now disclosed for the first time a method of forecasting a life-threatening condition comprising: a) providing measurement values for at least one vital sign parameter of an infant including at least one vital sign parameter other than a cardiac parameter; and b) generating a forecast of the onset of the life-threatening condition in the infant from said values in accordance at least in part with a temporal variation of at least one said vital sign parameter including said at least one vital sign parameter other than a cardiac parameter.

It is now disclosed for the first time a method of forecasting a life-threatening condition comprising: a) providing measurement values a classifier adapted to generate electrical output indicative of a forecast for the onset of a life-threatening condition in an infant; b) during a first time period, training said classifier using measurement values of at least one vital sign parameter collected for said infant; and c) using said trained classifier, generating a forecast of said onset of said life-threatening condition in said infant in accordance with measurement values of at least one said vital sign parameter for said infant for a subsequent time period.

According to some embodiments, at least one said vital sign parameter is other than a cardiac parameter According to some embodiments, said classifier forecasts said onset of said life-threatening condition in accordance with detected abnormalities in said measurement values during said subsequent period relative to said measurement values during said first time period.

It is now disclosed for the first time a method of forecasting a life-threatening condition comprising computing, from measurement values for at least one vital sign parameter of an infant for a first time period, a first function set of at least one function indicative of a normal physiological condition of said infant during said first time period; b) computing, from measurement values for at least one vital sign parameter of an infant for a subsequent time period, a second function set of at least one function indicative of a physiological condition of said infant during said second time period; c) generating a forecast of an onset of said life-threatening condition in accordance with physiological abnormalities during said subsequent time period detected in accordance with said first and second function set.

It is now disclosed for the first time a method of forecasting a life-threatening condition comprising: a) collecting time series measurement values of at least one vital sign parameter of an infant during a first time period (i.e. a "training period"); b) collecting time series measurement values of said at least one vital signs parameter of said infant during a subsequent time period; c) computing a comparison function of said time series values from said first and second time periods; and d) generating a forecast of the onset of the life-threatening condition in the infant from said values, wherein said forecast is determined at least in part by values of said comparison function.

According to some embodiments, at least one said vital sign parameter is other than a cardiac parameter.

It is now disclosed for the first time a method of forecasting a life-threatening condition comprising: a) providing measurement values of at least one vital sign parameter of an infant; b) normalizing said measurement values against historical values for said infant; c) generating a forecast of the onset of the life-threatening condition in the infant in accordance with results of said normalizing.

According to some embodiments, at least one said vital sign parameter is other than a cardiac parameter It is now disclosed for the first time a method of forecasting a life-threatening condition comprising: a) providing measurement values of at least one vital sign parameters, including at least one desaturation parameter, of an infant; and b) generating a forecast of the onset of the life-threatening condition in the infant from said values, wherein said forecast is determined at least in part by said measurement values for said at least one desaturation parameter.

It is now disclosed for the first time a method of forecasting a life-threatening condition comprising: a) providing measurement values for at least one vital sign parameter of an infant; and b) generating a forecast of the onset of the life-threatening condition in the infant from said values in accordance at least in part with a temporal variation of at least one said vital sign parameter, wherein said generating of said forecast includes performing at one least regression for time series values for at least one said vital sign parameter, and at least one said regression is performed to a non-constant function.

According to some embodiments, said forecast is generated at least in part in accordance with a relationship between a pre-determined value and a quality measurement of said regression to said non-constant function.

One non-limiting example of a "quality measurement" is the correlation of the linear regression.

According to some embodiments, an extent to which said forecast depends on results of said regression to said non-constant function depends on said quality measurement of said regression.

According to some embodiments, i) for a given said vital sign a plurality of regressions are performed; ii) said generated forecast depends at least in part on results of at least one said regression; and iii) a relationship between said generated forecast and results of a first said regression depends at least in part on a said quality parameter associated with a second said regression different from said first regression.

According to some embodiments, said regression is performed for at least one said vital sign parameter that is other than a cardiac parameter.

It is now disclosed for the first time a method of forecasting a life-threatening condition comprising a) providing measurement values for at least one vital sign parameter of an infant; b) computing a plurality of candidate prediction functions from said measurement values; c) computing a quality function (i.e. a parameter indicative of how good or accurate a forecast the candidate prediction function will yields) for each said candidate prediction function; and d) in accordance with values of at least one said candidate prediction function, generating a forecast of the onset of a life-threatening condition in said infant, wherein an extent to which a given said candidate prediction function governs results of said forecast is determined at least in part by said a value of a respective said quality function.

It is now disclosed for the first time a method of forecasting a life-threatening condition in a patient comprising: a) providing measurement values of a plurality of different vital sign parameters of a patient; b) generating a forecast of the life-threatening condition in the infant from said values, wherein said forecast is determined at least in part by said measurement values for each said vital sign parameter, and wherein, at least one of a first condition and a second condition conditions are true, wherein: I) according to said first condition: i) said generated forecast is determined at least in part by a location in parameter space having a boundary, and at least one said vital sign parameter has at least at least three threshold values one said boundary; ii) according to said second condition, said forecast is determined at least in part by a location in a parameter space having a boundary having a tangent that, at least one location, is oblique to a coordinate access of said parameter space.

It is noted that the present invention provides apparatus and computer-readable code for implementing any presently-disclosed method for forecasting a potentially life-threatening conditions.

It is now disclosed for the first time apparatus for forecasting a life-threatening condition in a premature infant, comprising: a) a data storage unit for storing measurement values for a plurality of vital sign parameter of an infant; and b) a data processing unit for generating a forecast of the life-threatening condition in the infant from said measurement values, wherein said data processing unit is operative such that said forecast is determined at least in part by said measurement values for each said vital sign parameter.

It is now disclosed for the first time apparatus for forecasting a life-threatening condition in an infant, the apparatus comprising: a) a data storage unit for storing measurement values of a plurality of different vital sign parameters of an infant including a temperature parameter, a desaturation parameter, a heart rate parameter, a bradycardia parameter, and a respiration rate parameter; and b) a data processing unit for generating a forecast of the life-threatening condition in the infant from said measurement values, wherein said data processing unit is operative such that said forecast is determined at least in part by said measurement values for each said vital sign parameter.

It is now disclosed for the first time apparatus for forecasting a life-threatening condition in an infant, the apparatus comprising: a) a data storage unit for storing measurement values for at least one vital sign parameter of an infant including at least one vital sign parameter other than a cardiac parameter; and b) a data processing unit for generating a forecast of the onset of the life-threatening condition in the infant from said values in accordance at least in part with a temporal variation of at least one said vital sign parameter including said at least one vital sign parameter other than a cardiac parameter.

It is now disclosed for the first time apparatus for forecasting a life-threatening condition in an infant, the apparatus comprising: a) a data storage unit for storing measurement values for at least one vital sign parameter of an infant; and b) a trainable classifier adapted to generate electrical output indicative of a forecast for the onset of a life-threatening condition in an infant after training, during a first time period, with measurement values of at least one vital sign parameter collected for said infant, said classifier operative to generate said forecast in said infant in accordance with measurement values of at least one said vital sign parameter for said infant for a subsequent time period.

It is now disclosed for the first time apparatus for forecasting a life threatening condition, the apparatus comprising: a) a data storage unit for storing measurement values for at least one vital sign parameter of an infant; and b) a data processing unit operative to: i) compute, from measurement values for at least one vital sign parameter of an infant for a first time period, a first function set of at least one function indicative of a normal physiological condition of said infant during said first time period; ii) compute, from measurement values for at least one vital sign parameter of an infant for a subsequent time period, a second function set of at least one function indicative of a physiological condition of said infant during said second time period; and c) generate a forecast of an onset of said life-threatening condition in accordance with physiological abnormalities during said subsequent time period detected in accordance with said first and second function set.

It is now disclosed for the first time apparatus for forecasting the onset of a life-threatening condition comprising: a) a data storage unit for storing: i) time series measurement values of at least one vital sign parameter of an infant during a first time period; and ii) time series measurement values of said at least one vital signs parameter of said infant during a subsequent time period; b) a data processing unit operative to i) compute a comparison function of said time series values from said first and second time periods; and ii) generate a forecast of the onset of the life-threatening condition in the infant from said values, wherein said forecast is determined at least in part by values of said comparison function.

It is now disclosed for the first time apparatus for forecasting a life-threatening condition, the apparatus comprising: a) a data storage unit for storing measurement values for at least one vital sign parameter of an infant; and b) a data processing unit operative to i) normalize said measurement values against historical values for said infant; and b) generate a forecast of the onset of the life-threatening condition in the infant in accordance with results of said normalizing.

It is now disclosed for the first time apparatus for forecasting for forecasting a life-threatening condition, the apparatus comprising: a) a data storage unit for storing measurement values for at least one vital sign parameter of an infant, including at least one desaturation parameter, of an infant; b) a data processing unit operative to generating a forecast of the onset of the life-threatening condition in the infant from said values, wherein said data processing unit is operative to determined said forecast at least in part by said measurement values for said at least one desaturation parameter.

It is now disclosed for the first time apparatus for forecasting for forecasting a life-threatening condition, the apparatus comprising: a) a data storage unit for storing measurement values for at least one vital sign parameter of an infant; and b) a data processing unit operative to generate a forecast of the onset of the life-threatening condition in the infant from said values in accordance at least in part with a temporal variation of at least one said vital sign parameter, wherein said data process is operative to generate said forecast includes performing at one least regression for time series values for at least one said vital sign parameter, and at least one said regression is performed to a non-constant function.

It is now disclosed for the first time apparatus for forecasting for forecasting a life-threatening condition, the apparatus comprising: a) a data storage unit for storing measurement values for at least one vital sign parameter of an infant; and b)

a data processing unit operative to i) compute a plurality of candidate prediction functions from said measurement values; ii) compute a quality function for each said candidate prediction function; iii) in accordance with values of at least one said candidate prediction function, generate a forecast of the onset of a life-threatening condition in said infant, wherein said data processing unit is operative such that an extent to which a given said candidate prediction function governs results of said forecast is determined at least in part by said a value of a respective said quality function.

It is now disclosed for the first time apparatus for forecasting a life-threatening condition in an infant, the apparatus comprising: a) a data storage unit for storing measurement values for a plurality of vital sign parameter of an infant; b) a data processing unit operative to generate a forecast of the life-threatening condition in the infant from said values, wherein said data processing unit is operative such that said forecast is determined at least in part by said measurement values for each said vital sign parameter, and wherein, at least one of a first condition and a second condition conditions are true, wherein: I) according to said first condition: i) said generated forecast is determined at least in part by a location in parameter space having a boundary, and at least one said vital sign parameter has at least at least three threshold values one said boundary; ii) according to said second condition, said forecast is determined at least in part by a location in a parameter space having a boundary having a tangent that, at least one location, is oblique to a coordinate access of said parameter space.

It is noted that the "data storage unit" may be implemented using any combination of volatile and non-volatile memory.

It is noted that "accessing data" or "accessing values" typically includes the step of reading data (for example, measurement values) from volatile and/or non-volatile memory.

It is now disclosed for the first time a computer readable medium comprising program instructions, wherein when executed the program instructions are operable to: a) access measurement values for at least one vital sign parameter of an infant; b) generate a forecast of the life-threatening condition in the infant from said measurement values, wherein said data processing unit is operative such that said forecast is determined at least in part by said measurement values for each said vital sign parameter.

It is now disclosed for the first time a computer readable medium comprising program instructions, wherein when executed the program instructions are operable to: a) access measurement values of a plurality of different vital sign parameters of an infant; b) generate a forecast of the life-threatening condition in the infant from said values, wherein said forecast is determined at least in part by said measurement values for each said vital sign parameter.

It is now disclosed for the first time a computer readable medium comprising program instructions, wherein when executed the program instructions are operable to: a) access measurement values of a plurality of different vital sign parameters of an infant including a temperature parameter, a desaturation parameter, a heart rate parameter, a bradycardia parameter, and a respiration rate parameter; and b) generate a forecast of the life-threatening condition in the infant from said values, wherein said forecast is determined at least in part by said measurement values for each said vital sign parameter.

It is now disclosed for the first time a computer readable medium comprising program instructions, wherein when executed the program instructions are operable to: a) access measurement values for at least one vital sign parameter of an infant including at least one vital sign parameter other than a cardiac parameter; b) generate a forecast of the onset of the life-threatening condition in the infant from said values in accordance at least in part with a temporal variation of at least one said vital sign parameter including said at least one vital sign parameter other than a cardiac parameter.

It is now disclosed for the first time a computer readable medium comprising program instructions, wherein when executed the program instructions are operable to: a) provide a classifier adapted to generate electrical output indicative of a forecast for the onset of a life-threatening condition in an infant; b) during a first time period, train said classifier using measurement values of at least one vital sign parameter collected for said infant; c) using said trained classifier, generate a forecast of said onset of said life-threatening condition in said infant in accordance with measurement values of at least one said vital sign parameter for said infant for a subsequent time period.

It is now disclosed for the first time a computer readable medium comprising program instructions, wherein when executed the program instructions are operable to: a) compute, from measurement values for at least one vital sign parameter of an infant for a first time period, a first function set of at least one function indicative of a normal physiological condition of said infant during said first time period; b) compute, from measurement values for at least one vital sign parameter of an infant for a subsequent time period, a second function set of at least one function indicative of a physiological condition of said infant during said second time period; c) generate a forecast of an onset of said life-threatening condition in accordance with physiological abnormalities during said subsequent time period detected in accordance with said first and second function set.

It is now disclosed for the first time a computer readable medium comprising program instructions, wherein when executed the program instructions are operable to: a) access time series measurement values of at least one vital sign parameter of an infant during a first time period; b) access time series measurement values of said at least one vital signs parameter of said infant during a subsequent time period; c) compute a comparison function of said time series values from said first and second time periods; and d) generate a forecast of the onset of the life-threatening condition in the infant from said values, wherein said forecast is determined at least in part by values of said comparison function.

It is now disclosed for the first time a computer readable medium comprising program instructions, wherein when executed the program instructions are operable to: a) access measurement values of at least one vital sign parameter of an infant; b) normalize said measurement values against historical values for said infant; c) generate a forecast of the onset of the life-threatening condition in the infant in accordance with results of said normalizing.

It is now disclosed for the first time a computer readable medium comprising program instructions, wherein when executed the program instructions are operable to: a) provide measurement values of at least one vital sign parameters, including at least one desaturation parameter, of an infant; b) generate a forecast of the onset of the life-threatening condition in the infant from said values, wherein said forecast is determined at least in part by said measurement values for said at least one desaturation parameter.

It is now disclosed for the first time a computer readable medium comprising program instructions, wherein when executed the program instructions are operable to: a) access measurement values for at least one vital sign parameter of an infant; b) generate a forecast of the onset of the life-threatening condition in the infant from said values in accordance at least in part with a temporal variation of at least one said vital sign parameter, wherein said generating of said forecast includes performing at one least regression for time series values for at least one said vital sign parameter, and at least one said regression is performed to a non-constant function. It is now disclosed for the first time a computer readable medium comprising program instructions, wherein when executed the program instructions are operable to: a) access measurement values for at least one vital sign parameter of an infant; b) compute a plurality of candidate prediction functions from said measurement values; c) compute a quality function for each said candidate prediction function; d) in accordance with values of at least one said candidate prediction function, generate a forecast of the onset of a life-threatening condition in said infant, wherein an extent to which a given said candidate prediction function governs results of said forecast is determined at least in part by said a value of a respective said quality function. It is now disclosed for the first time a computer readable medium comprising program instructions, wherein when executed the program instructions are operable to: a) access measurement values of a plurality of different vital sign parameters of a patient; b) generate a forecast of the life-threatening condition in the infant from said values, wherein said forecast is determined at least in part by said measurement values for each said vital sign parameter, and wherein, at least one of a first condition and a second condition conditions are true, wherein: I) according to said first condition: i) said generated forecast is determined at least in part by a location in parameter space having a boundary, and at least one said vital sign parameter has at least at least three threshold values one said boundary; ii) according to said second condition, said forecast is determined at least in part by a location in a parameter space having a boundary having a tangent that, at least one location, is oblique to a coordinate access of said parameter space.

These and further embodiments will be apparent from the detailed description and examples that follow.

DETAILED DESCRIPTION

Figure 1:
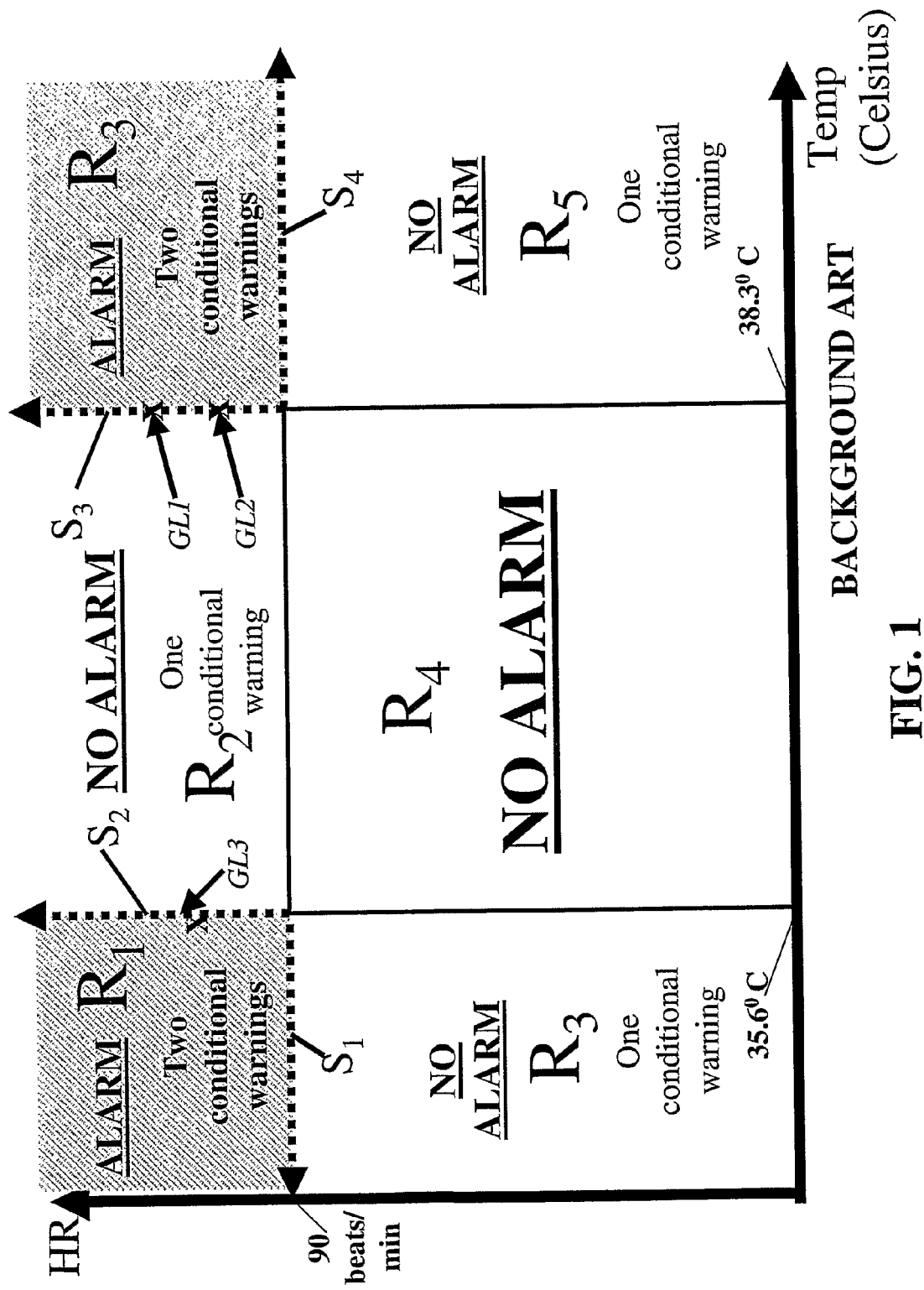
FIG. 1 provides an illustration of the partitioning of a parameter space into regions where an alarm for sepsis is generated, and regions where an alarm for sepsis is not generated (prior art).

The present invention will now be described in terms of specific, example embodiments. It is to be understood that the invention is not limited to the example embodiments disclosed. It should also be understood that not every feature of the system, method and computer-readable code for forecasting the onset of the potentially life-threatening condition is necessary to implement the invention as claimed in any particular one of the appended claims. Various elements and features of devices are described to fully enable the invention. It should also be understood that throughout this disclosure, where a process or method is shown or described, the steps of the method may be performed in any order or simultaneously, unless it is clear from the context that one step depends on another being performed first.

Introduction

The present inventor is disclosing a method, apparatus and computer readable code for forecasting the onset of potentially life-threatening condition (for example, sepsis). In particular, the presently disclosed methods, apparatus and computer readable code are useful for forecasting the onset of the potentially catastrophic illness in infants, such as very low birthweight and pre-mature infants.

One example of a potentially catastrophic condition is sepsis. To date, sepsis is typically detected and prognosticated worldwide by clinical examination.

In some embodiments, "forecasting" a life-threatening condition includes forecasting the onset of the life-threatening condition. Forecasting the onset of the life-threatening condition includes generating an electrical signal or output indicative of a likelihood (either a numerical indication or a "Boolean" yes/no indication) that the life-threatening condition will occur in the patient in the future. In experiments conducted using apparatus configured in accordance with exemplary embodiments of the present invention, it was possible to forecast the onset of late-onset sepsis between 18 and 40 hours in advance. Thus, in exemplary embodiments, "forecasting" (or "generating a forecast for") the onset of the life-threatening condition may refer to forecasting at least 12 hours, at least 18 hours, at least 24 hours, and/or at least 36 hours before onset of the condition. It is appreciated that forecasting the "onset" of the condition also refers to the forecasting the "lack of expected onset" of the condition.

In some embodiments, "forecasting" the life-threatening condition includes forecasting the severity of the life-threatening condition. Thus, in some embodiments, an electrical signal indicative of the severity of the life-threatening signal is created.

The forecast is generated from one or more measurement values of one or more vital sign parameters. As used herein, a "measurement value" of a given vital sign parameter is a value that is indicative of an actual measured value for a given vital sign parameter for a single time and/or for a plurality of times.

In exemplary embodiments, a forecast is generated for a potentially catastrophic or life-threatening illness or condition. In exemplary embodiments, this life-threatening illness or condition is an infectious disease such as sepsis. Nevertheless, other embodiments are also contemplated by the present invention. For example, the presently disclosed techniques may be used to forecast the onset of a life-threatening condition due to lung immaturity or underdevelopment.

Embodiments of the present invention may be characterized by one or more of the following features:

a) generating a forecast for the potentially catastrophic illness from measurement values for a plurality of vital signs. Exemplary vital signs include but are not limited to;
  i) a breathing parameter—for example, a respiration rate, a statistical moment of respiration rate—for example, variance which may be indicative of an apnea condition.
  ii) metabolic-related parameters such as body temperature;
  iii) cardiac parameters such as heart rate and frequency of bradycardia events;
  iv) desaturation parameters and other blood-related parameters;
  v) blood pressure;
  vi) parameters indicative of food digestion—for example, material obtained from the infant's GI tract may be analyzed.
b) computing functions (for example, regression functions) indicative of a trend of one or more vital signs, and then generating a forecast in accordance with one or more computed trend(s);
c) computing a function indicative of normal physiological behavior for a particular patient, and then subsequently generating a forecast in accordance with detected abnormalities relative to the computed normal physiological behavior. In some embodiments, the "function indicative of normal physiological behavior" may be updated over time;
d) normalizing one or more values of vital signs relative to reference parameters (for example, pre-defined, well known parameters). In some embodiments, measurement values for one or more vital sign may be normalized relative to a patient or infant status parameter or "reference parameters," such as age or weight of the patient.
e) normalizing one or more values of vital signs relative to historical values. Not all parameters need to be normalized using the same normalization function, or need to be normalized at all—in one example, the desaturation frequency is normalized relative to historical values (for the particular patient), while a bradycardia factor not normalized relative to historical values);
f) for a given set of one or more vital signs, computing a plurality of "candidate" indicators of behavior of the vital sign (for example, "trend" indicators and/or central tendency indicators such as average, standard deviation or higher order statistical moments), and then selecting a 'better' indicator (what appears to be a more "meaningful" function of measured values of vital sign parameters) in accordance with pre-defined criteria.

As used herein, an "age" of an infant may refer to either the gestational age of the baby (i.e. the time since conception) or the birth age (i.e. time since birth), or any function of the gestational age and the birth age. Although not a limitation, typically the "age" is the gestational age.

The presently disclosed methods, apparatus, and computer readable code are useful for forecasting the onset of a life-threatening condition in any patient, including infants and older patients. Nevertheless, it is noted that the presently disclosed methods, apparatus, and computer readable code are particularly useful for predicting the onset of disease in very low birthweight infants.

Not wishing to be bound by any particular theory, the present inventors are now disclosing that low birthweight infants may tend to have relatively immature regulatory systems. As such, the physiology as well as the behavior of measured vital sign parameters may vary between infants, making it difficult to draw conclusions for one infant based on observations in another infant. For example, in one particular infant, a certain set of measured values for one or more physiological parameters may be indicative of the onset of a certain life-threatening condition, while in another infant the same or similar measured values may be indicative of the lack thereof, or may be inconclusive.

As such, although not a limitation of the present invention, it may be useful, for example, to determine what is "normal" for a particular infant (for example, by "training" a classifier on the particular infant for which a forecast is to be made, and only on other infants from a training set), and then to forecast the onset of the disease if "abnormal" values and/or trends are detected.

Furthermore, although not a limitation of the present invention, it may be useful to determine "on the fly" if an observed set of values for one or more vital sign parameters, or an observed trend for the one or more vital sign parameters is meaningful. Thus, when generating the forecast, certain "candidate trends" or "candidate central tendencies" may be emphasized, de-emphasized and/or discarded (i.e. using some sort of weighting function) in accordance with a "quality measurement" of the trend or central tendencies. In one non-limiting example, for a given vital sign parameter, a correlation coefficient of time series values of a vital sign parameter is compared with a pre-determined value. According to this particular example, if the correlation coefficient exceeds the pre-determined value, the forecast is generated at least in part in accordance with an associated linear regression.

As used herein, a "time series" of a refers to a value of vital sign parameter (or function thereof) at either a single point in time, or at a plurality of points in time Furthermore, although not a limitation of the present invention, it may be useful to generate a prediction in accordance with a plurality of distinct vital sign parameters. Not wishing to be bound by theory, it is noted that use of the plurality of vital sign parameters may reduce "noise" associated with any single vital sign parameters (for example, due to an immature regulatory system of the infant). Although not a limitation, it is noted that this may be especially useful when handling low birthweight infants with relatively undeveloped regulatory systems.

Once again, not wishing to be bound by any particular thereby, use of values for the plurality of vital sign parameters (and also, from a plurality of physiological systems) may be useful for situations where a "signal" associated with one or more individual vital sign parameters is inconclusive, but specific combinations of values of the vital sign parameters may indeed be indicative of the future presence (or absence) and/or onset (or lack thereof) of the potentially life-threatening or catastrophic condition.

Once again, not wishing to be bound by theory, it is disclosed that it may be useful in certain embodiments to capitalize on particular "synergies" between different vital signs when predicting the onset of the potentially catastrophic condition, and thus to generate predictions in accordance with measurement values of a plurality of different vital signs.

Thus, there are many instances where it may be desired to generate a forecast based on measurement values of vital sign parameters from a plurality of different physiological systems, because, for example the onset (or lack thereof) of the life-threatening condition may be associated with a plurality of physiological systems, and not just a single physiological system. Exemplary physiological systems include but are not limited to the cardiovascular system (associated with, for example, cardiac parameters such as the heart rate and the frequency of bradycardia), the respiratory system (associated with respiration rate), the muscular system (for example, a body temperature parameter), and the skin (for example, a body temperature parameter and a desaturation parameter).

Not wishing to be bound by theory, it is noted that some parameters, particularly those related to skin, may be indicative of a homeostasis relationship between the patient and the external environment. Values of these parameters and trends in these parameters may foreshadow the future presence of the life-threatening condition.

Exemplary Procedure for Forecasting a
Life-Threatening Condition

Figure 2:
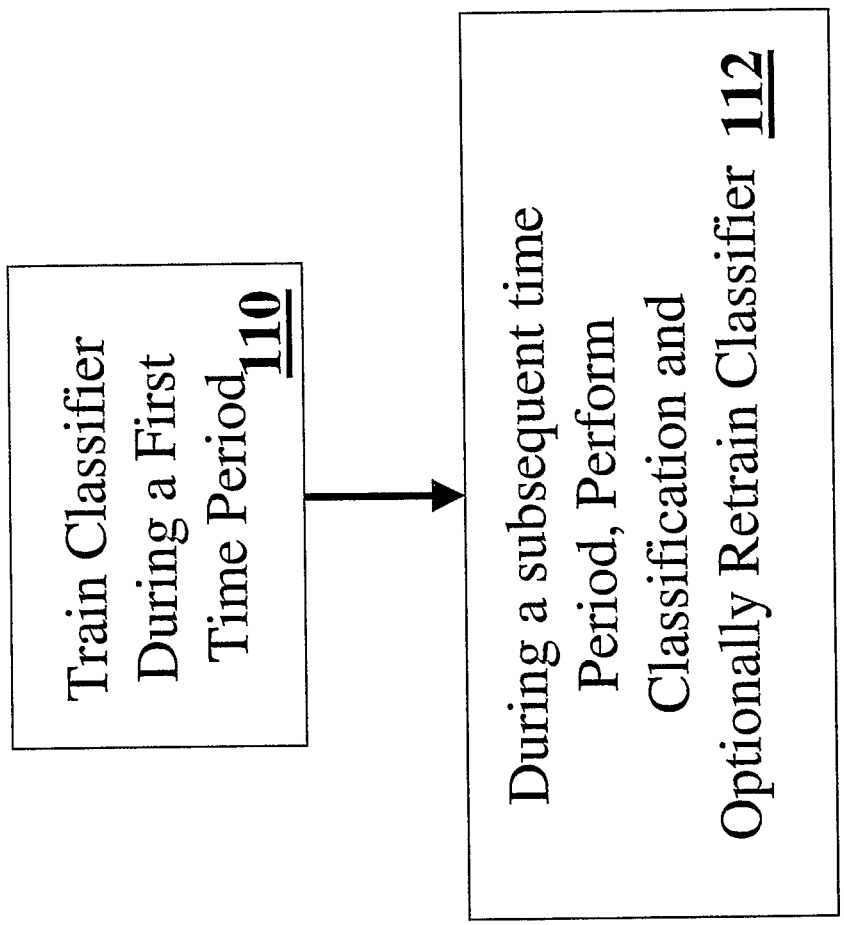
FIG. 2 provides a flow chart describing an exemplary procedure for forecasting a life-threatening condition, where a classifier is trained and then a used to perform classification, in accordance with some embodiments of the present invention.

FIG. 2 provides a flow chart describing an exemplary procedure for forecasting a life-threatening condition, where a classifier is trained and then a used to perform classification, in accordance with some embodiments of the present invention, The term "classifier" refers to any combination of software and/or hardware capable of "classifying" input data (for example, measurement value(s) for one or more vital sign parameters, for a given time or period of time) to generate a forecast for the onset (or lack thereof) of the life-threatening condition. The generation of the forecast is the "classifying" of the input data. The "classification" or "generated forecast" may be provided as any electrical signal. The term "classification" is not limited to the specific case where a discrete value is selected from a plurality of values.

The classifier may be a "heuristic classifier" (for example, implemented "hard coded" values provided a human expert), a "statistical classifier" (for example, generated in accordance with "training set data") or any combination thereof.

Thus, in some embodiments, the classifier may be "trained" using data from a "training set" patients (i.e. other than the patient for which a forecast is to be generated). Alternatively or additionally, the classifier may be "trained" using historical data of the particular patient. Trainable classifiers are well known in the art, and may, for example, be based on any combination of neural networks, decision trees, decision tables, Markov models, regression models, meta-learning algorithms, or other techniques familiar to the skilled artisan.

Referring once more to FIG. 2, it is noted that in one example, one may generate a forecast by first training the classifier to "recognize" physiological norms for a given patient 110, and then, during a subsequent time period, by forecasting 112 (for example, by classifying measurement value data) the onset of the life-threatening condition by detecting deviations from the norm and/or abnormalities for a given patient. During this subsequent time period, the classifier is optionally re-trained (i.e. the concept of a "normal" physiological state may change as a function of time, and may be updated).

Figure 3:
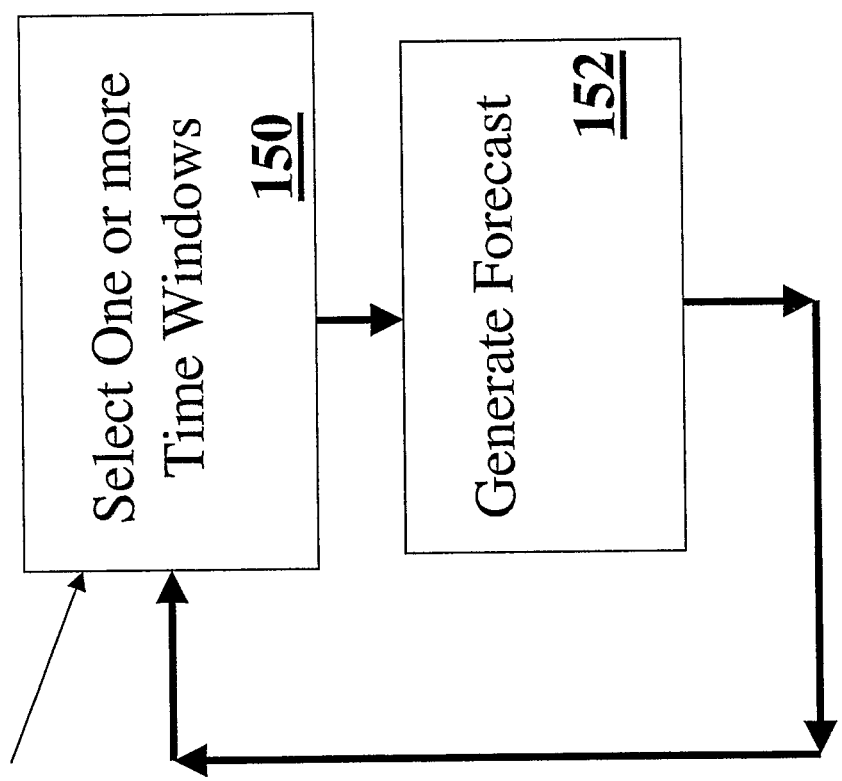
FIG. 3 provides a flow chart describing an exemplary procedure for forecasting a life-threatening condition using a "sliding window" procedure in accordance with some embodiments of the present invention.

FIG. 3 provides a flow chart describing an exemplary procedure for forecasting a life-threatening condition using a "sliding window" procedure in accordance with some embodiments of the present invention. A given time window is selected 150, and for the time window, a forecast is generated 152. This procedure may be repeated one or more times. Thus, FIG. 3 describes a "sliding window" forecast procedure.

Figure 4:
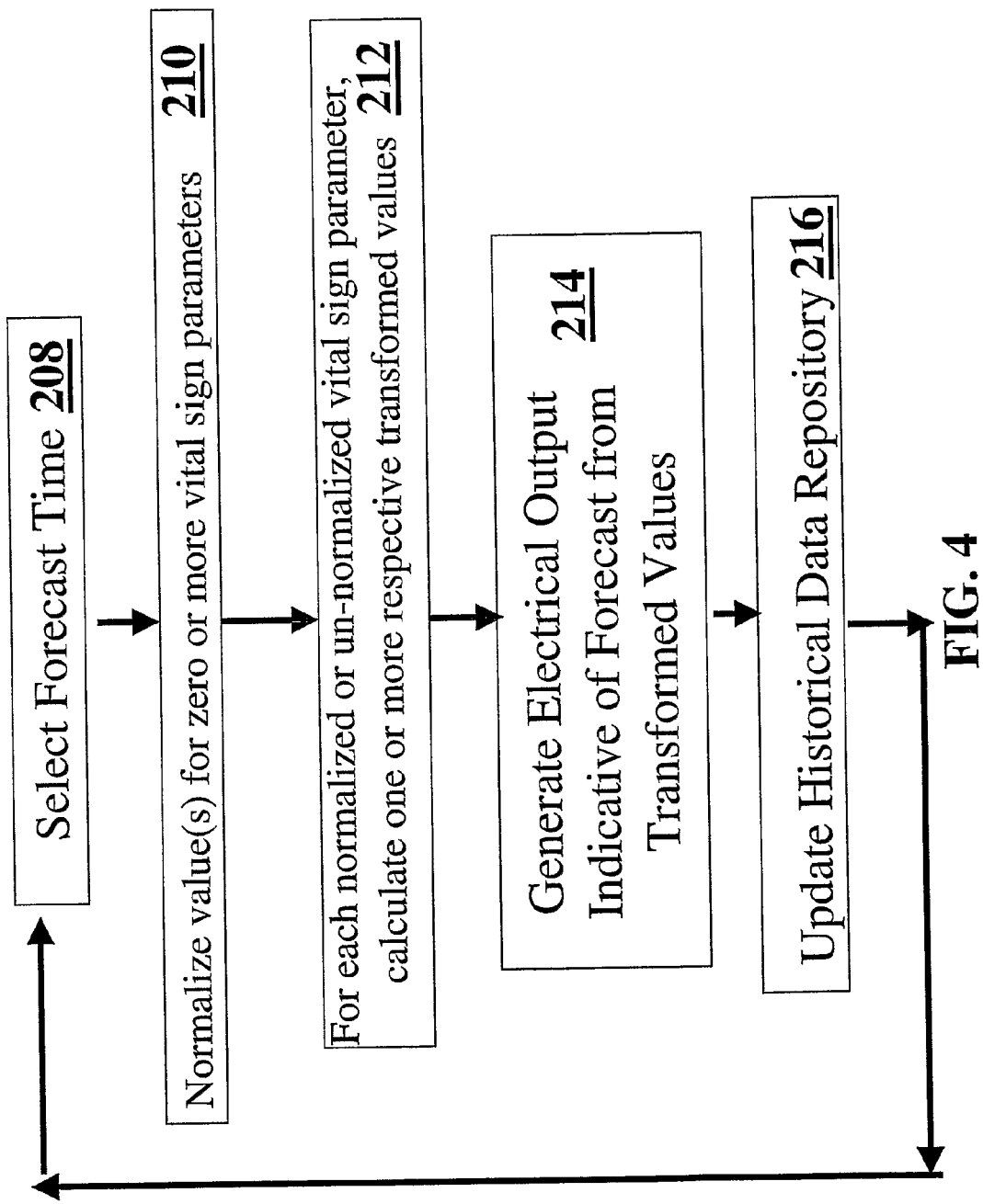
FIG. 4 provides a flow chart describing an exemplary procedure for forecasting a life-threatening condition for at least one forecast time in accordance with some embodiments of the present invention.

FIG. 4 provides a flow chart describing an exemplary procedure for forecasting a life-threatening condition for at least one forecast time in accordance with some embodiments of the present invention. For each selected 208 forecast time, values of zero, one or more vital sign parameters may be normalized.

In one example, the body temperature (measured anywhere on, near, or in the patient's body) may be normalized 210 in accordance with the patient's weight and/or age in accordance with established medical norms.

In some examples relating to forecasting from a plurality of vital signs, different vital signs may be normalized differently. For example, heart rate may be normalized using a different procedure than body temperature.

For each normalized or un-normalized vital sign parameter, one or more respective transformed values 212 may optionally be calculated. This simplest transformation, the identity transformation, does not require any calculation.

In some embodiments, these transformed values are statistically derived, and may reflect a "meaningful indication" of the respective raw vital sign parameter, though this is not a limitation of the present invention. For some vital sign parameters, it may not be necessary to calculate a transformed value (i.e. the transformed value is identical to the raw value, and the "transformation" is the identity transformation). In some embodiments, each vital sign parameter is transformed separately, irrespective of other vital sign parameters, though this is not a limitation.

Once the transformed values are obtained (or once it is decided to use one or more "raw" untransformed values for one or more vital signs), it is possible to generate 214 an output indicative of a forecast of the onset (or lack thereof) of the life-threatening condition, using any technique known in the art for "combining" factors with predictive power (for example, heuristics, statistics from a training set of other patients, other methods known to the skilled artisan, or any combination thereof). Some aspects of generating a forecast from measurement values for a plurality of different vital signs are explained below.

It is noted that in some embodiments, future forecasts may be made in accordance with historical forecasts and/or historical values for one or more vital sign parameters. Thus, in some embodiments, a historical data repository is optionally updated 216 for use in future forecasts.

Figure 5:
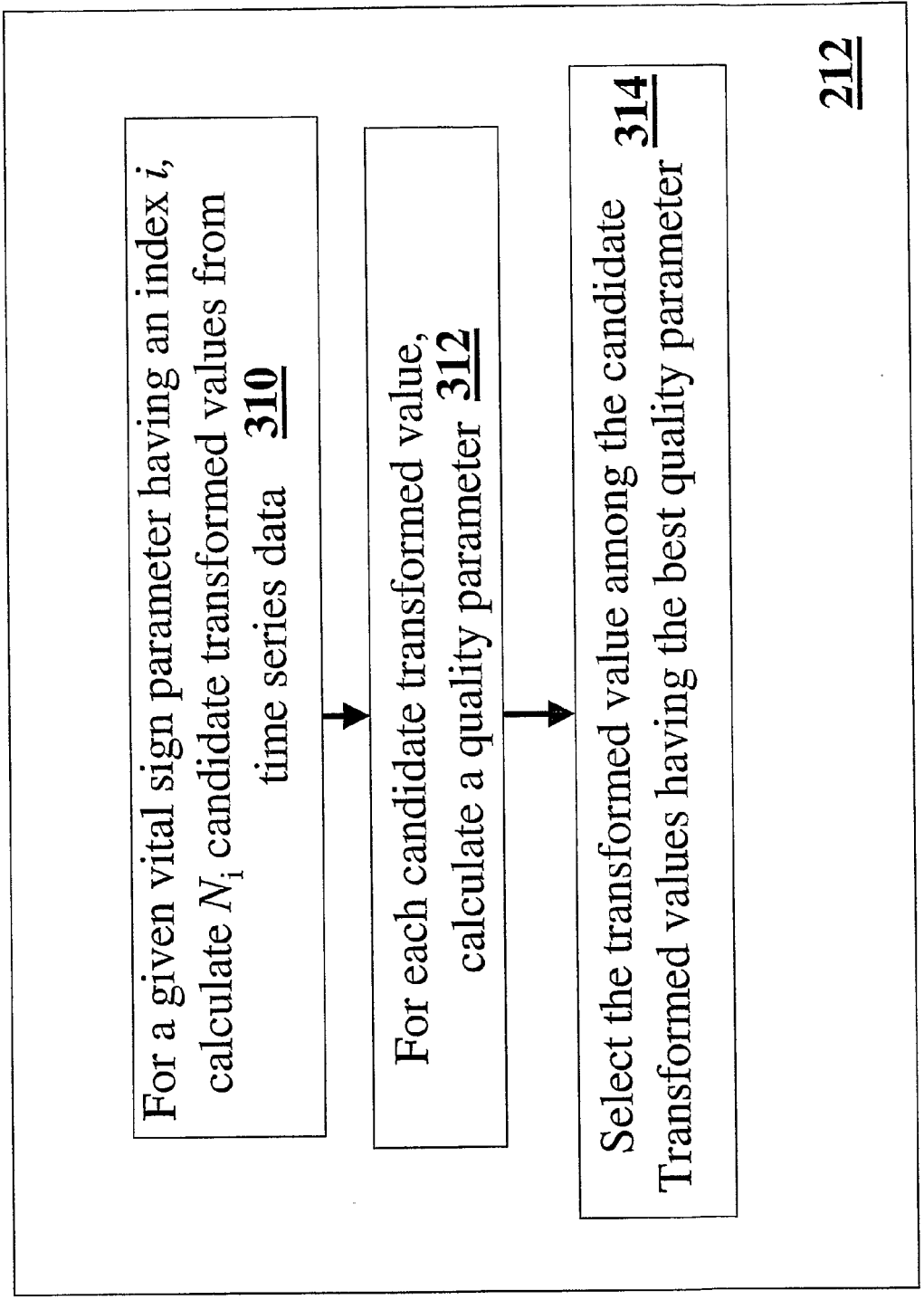
FIG. 5 provides a flow chart describing an exemplary procedure for computing a transformed value of values of a vital sign parameter in accordance with some embodiments of the present invention.

FIG. 5 describes an exemplary, non-limiting procedure for generating or calculating 212 transformed values for a given vital sign parameter. For the given vital sign parameter (i.e. at a single time, or continuous time interval, or at a plurality of discrete times), one or more "candidate" transformations may be obtained, for example transformations obtaining value(s) reflecting a trend or central tendency (for example, a statistical moment of the time series data) or any "meaningful" representation of the raw values of the vital sign parameter. After carrying out a plurality of "candidate" transformations, the transformation associated with the more "meaningful" representation of the vital sign parameter may be selected 314, for example, in accordance with a calculated "quality" parameter 312 for a measured value (or values at a plurality of times) of the given vital sign parameter. One non-limiting example of a "quality" parameter is a "goodness of fit" of the linear regression (i.e. a function of residuals between the function to which the time series data is being fit, and the time series data itself).

In exemplary embodiments, one or more outliers may be discarded.

Figure 6A:
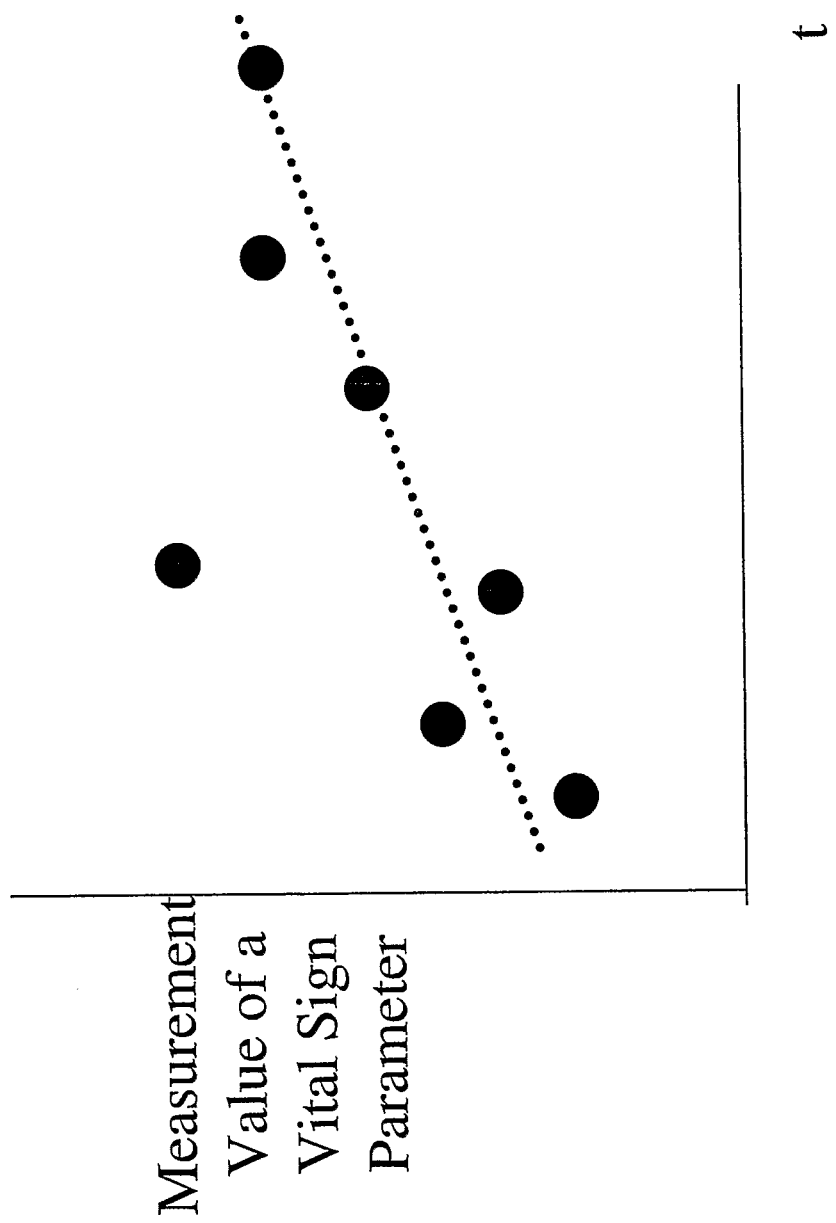
FIGS. 6A and 6B relate to exemplary candidate transformations for extracting a meaningful representation from a time series of measurement values for a given vital sign parameter.
Figure 6B:
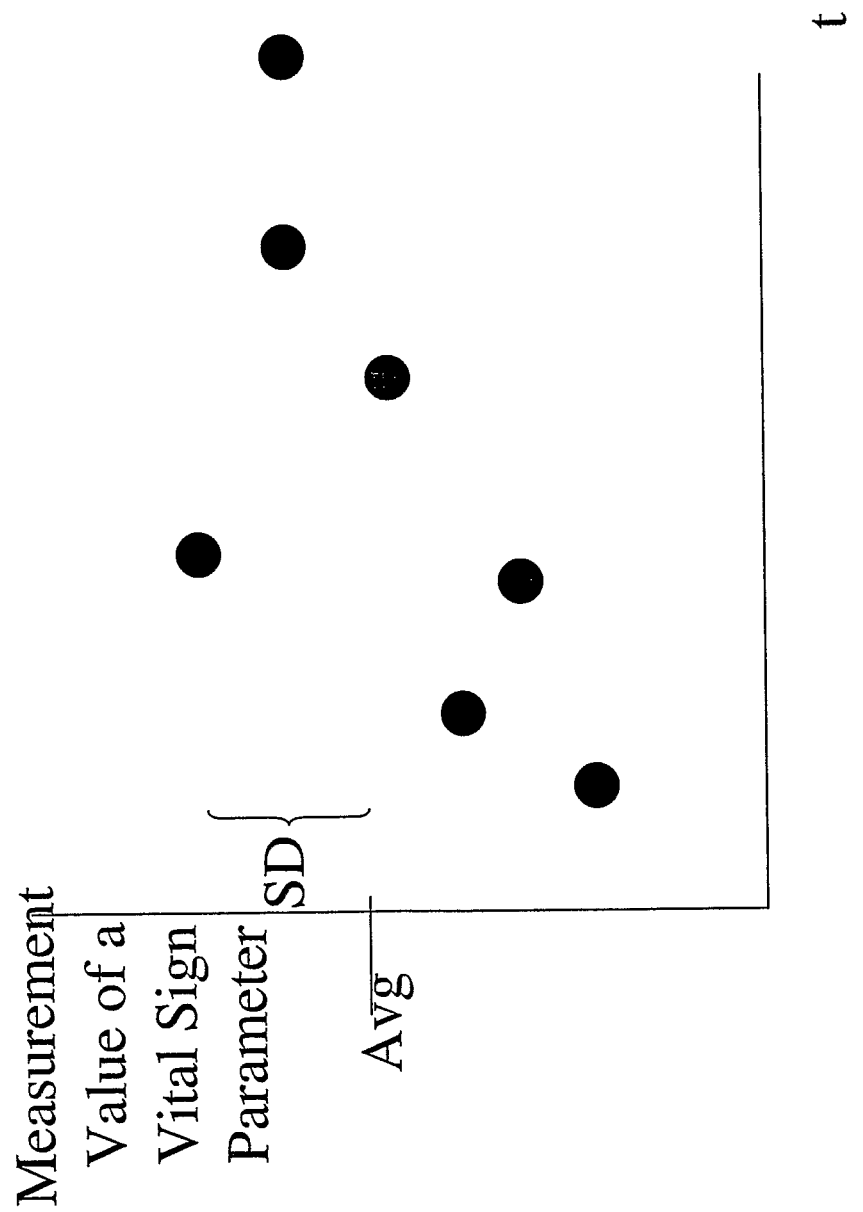

FIGS. 6A and 6B relate to exemplary candidate transformations for extracting a "meaningful" representation from a time series of measurement values for a given vital sign parameter. A "candidate" transformation of measurement values refers to a transformation of measurement values which may or may not be used in subsequently generating the forecast (i.e. may be used or "discarded").

In FIG. 6A, the transformed parameter may be a slope or other parameter associated with a regression (for example a linear regression). The "quality parameter" is indicative of the "goodness of fit" of the linear regression.

Although FIG. 6A was explained in terms of a linear function, it is appreciated that regression to any other functional form (including but not limited to a non-linear functional form) (i.e. function relating a measurement value of one or more vital sign parameters) may be appropriate. In exemplary embodiments, this function is a "non-constant" (for example, a line that is not a constant).

Alternatively or additionally, as shown in FIG. 6B, a central tendency of time series data (For example, a statistical moment such as an average or a standard deviation) may be computed. In one particular example, the following rule may be used: if the correlation of a linear regression (i.e. see FIG. 6A) exceeds a pre-defined value, then a transformed value related to the regression is selected from the candidate transformed values, while the average and/or standard deviation of the time series may be de-emphasized or discarded.

This physically corresponds to the case where a physiological parameter follows a specific trend, and it is decided that the trend may be more meaningful for forecasting the onset of the potentially life-threatening condition than the absolute values of the measured or measurement values of the physiological parameter.

Referring once again to FIG. 5, it is noted that in some embodiments, values for individual vital sign parameters are individually normalized 212, and then are used in combination with each other 214 to generate the forecast (i.e. electrical output indicative of the forecast).

Threshold Values

In some embodiments, a generated forecast may be determined at least in part by a relation between a measured value of a given vital sign parameter (for a single time or for a plurality of times) and at least one "threshold" value.

In particular, for some values of the given vital sign parameter, a "first forecast" (indicating that the likelihood of the onset of the potentially life threatening condition is a first likelihood (and/or predicted severity) value (i.e. indicative of a probability), or a likelihood value greater than the first likelihood value) may be generated, while for other values of the given vital sign parameter a "second forecast" (indicating that the likelihood of the onset of the potentially life threatening condition is a second value less than the first value, or a value less than the second value) may be generated. A threshold value for a given vital sign for the first and second likelihood values (where the first likelihood value is greater than the second likelihood value) is defined as follows:

a) there exists at least one first measured value of the given vital sign where the difference between the first measured value of the given vital sign and the threshold value is a given sign (i.e. less than zero, or greater than zero) (i.e. this may be thought of as on "one side" of the boundary given by the threshold value)

b) there exists at least one second measured value of the given vital sign where the difference between the second measured value of the given vital sign and the threshold value is the opposite sign of the given sign (i.e. this may be thought of as on "the opposite side" of the boundary given by the threshold value)

c) for the first measured value of the given vital sign, the generated forecast is indicative of a likelihood of the onset of the potentially life threatening condition that is at least the first likelihood value;

d) for the second measured value of the given vital sign, the generated forecast is indicative of at a likelihood of the onset of the potentially life threatening condition that is at most the second likelihood value.

It is noted that this threshold value need not be "explicitly" defined within the apparatus for generating the forecast, and the aforementioned discussion of "threshold value" merely describes the apparatus behavior and sensitivity to measurement values of the vital sign parameters.

It is noted that for a given vital sign for the first and second likelihood values (where the first likelihood value is greater than the second likelihood value) there may, in some situations, be more than one threshold value, or more than two threshold values.

As will be discussed more in depth in the next section, it is possible to map between parameter space (i.e. the inputs—measured values indicative of values of vital sign parameters) and prediction values (i.e. likelihood values and/or predicted severity values). Any time there is a "border" between two different regions (for example, R6, and R7) in parameter space defining two generated likelihood values (i.e. a probability) or two generated predicted severity values, and the border is not parallel to the to an axis associated with a given vital sign parameter at a given location, then the value of the vital sign parameter at the "given location" is a "threshold value."

This may be explained further with reference to FIG. 1 and FIG. 7S. In FIG. 1, given location GL1 is located on curve S3 which is a border in parameter space between the prediction associated with region R2 and the prediction associated with region R3. The value of the vital sign parameter "temperature" at GL1 is 38.3 degrees C. Thus, 38.3 degrees C. is considered a "threshold value" for the prior art apparatus and method of FIG. 1. Similarly, at GL2, the vital sign parameter "temperature" at GL1 is 38.3 degrees C. Given location GL3 of FIG. 1 is located on curve S2 which is a border in parameter space between the prediction associated with region R1 and the prediction associated with region R2. The value of the vital sign parameter "temperature" at GL3 is 35.6 degrees C. Thus, 35.6 degrees C. is considered a "threshold value" for the prior art apparatus and method of FIG. 1. It is noted that for the prior art described in FIG. 1, for the vital sign parameter "body temperature" there are only two threshold parameters—35.6

Figure 7A:
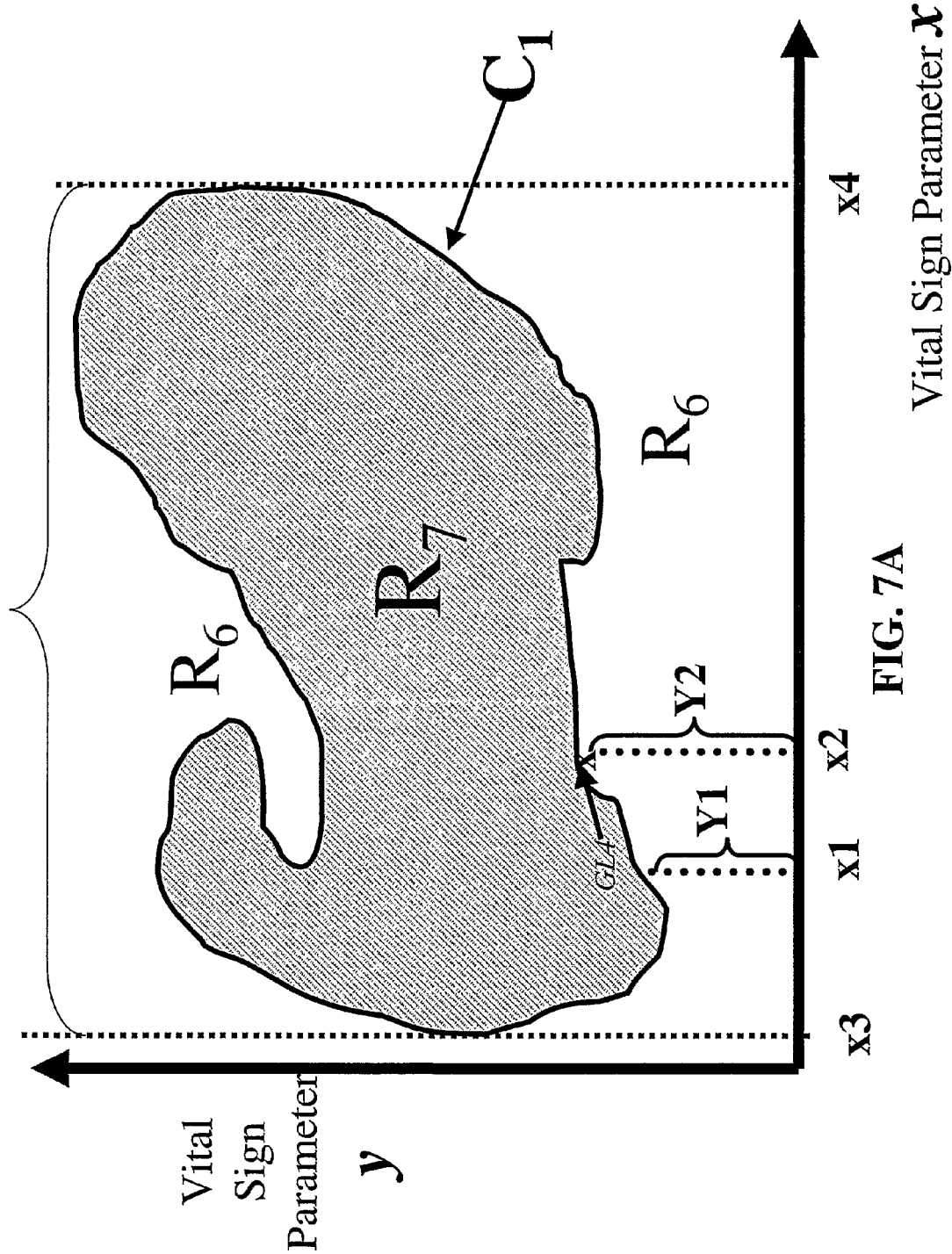
FIG. 7A provides an illustration of partitioning a parameter space in accordance with values indicative of a forecasted severity and/or forecasted likelihood of an onset of a potentially life-threatening condition in accordance with some embodiments of the present invention.

Referring to FIG. 7A, given location GL4 is located on curve C1 which is a border in parameter space between the prediction (i.e. forecast of a likelihood or the condition and/or a forecasted severity) associated with region R6 and the prediction associated with region R7. The value of the "vital sign parameter X" at GL4 is x2.

In the example of FIG. 7A, every value between x3 and x4 is thus a threshold value.

In summary, a value of a vital sign parameter is a "threshold value" for the vital sign parameter if there exists a border (an N-1 dimensional manifold for an N-dimensional parameter space) between two regions of parameter space, each region being associated with a different forecast (likelihood and/or predicted severity) for the potentially life-threatening condition such that there is a point on the border with the threshold value for the vital sign parameter.

Threshold Values and Predictions Generated in Accordance with a Plurality of Vital Signs It is noted that for embodiments where the forecast is generated in accordance with a plurality of vital signs, the operative "threshold value" for a given vital sign for given first and second likelihood values may depend on the measured values of vital signs other than the given vital sign.

An example of this is illustrated graphically in FIG. 7A. It is noted that FIG. 7A relates to the particular case of only two vital sign parameters, which was selected for ease of illustration. Typically, more than two vital sign parameters will be used, though embodiments where only two vital sign parameters are used are also within the scope of the present invention. Furthermore, it is note that FIG. 7A is a "snapshot" of various regions at a given instant in time. In exemplary embodiments, the border between various regions (for example, curve $C_1$ between regions $R_6$ and $R_7$) may vary as a function of time. In the alternate, embodiments where, for at least one time interval, the border between various regions (for example, curve $C_1$ between regions $R_6$ and $R_7$) remains fixed are also contemplated by the present invention.

In region R6, a forecast associated with a likelihood that is associated with at least a likelihood value L6 is generated, while in region R7, a forecast associated with a likelihood that is associated with at most a likelihood value L7 is generated.

The boundary between R6 and R7 is given by a curve C1. It is noted that curve C1 may have a tangent that is oblique to the coordinate axes of parameter space at different locations along C1.

When measured values of vital sign parameter x and vital sign parameter y (for one time, or for a plurality of times) are determined, this is associated with a given location in the "parameter space" defined by the coordinate axes.

The threshold value for vital sign parameter y for likelihoods L6 and L7 is given by a distance between the horizontal axis and the curve C1. As noted before, there may be more than one threshold value for a given vital sign parameter for given first and second likelihood values (for example, L6 and L7), and as such, the "distance" between curve C1 and a given axis (for example, horizontal axis) is not necessarily a unique number.

It is noted that this distance (and hence the threshold parameters for L6 and L7) between the curve and the axis may vary in accordance with a location in parameter space determined by a vital sign parameter other than vital sign parameter y (for example, vital sign parameter x). Thus, the operative "threshold value" (i.e. which location on C1 is operative to characterize behavior of the forecast apparatus relative to a measured value for vital sign parameter y) of a given vital sign parameter may vary in accordance with measured value of vital sign parameter x.

It is noted that FIG. 7A relates to the special case of two vital sign parameters, and the parameter space is a two dimension space, where boundaries between different regions are given by one dimensional curves. For cases where there are three or more vital sign parameters, the parameter space may be given by a higher dimensional space, and the boundaries may be given by surfaces, planes, hyper-planes, etc.

Furthermore, in the example of FIG. 7A, the threshold value associated with a certain vital sign parameter (i.e. vital sign parameter x) depends on a measured value of exactly one other vital sign parameter (i.e. vital sign parameter y). This is not to be construed as a limitation, and in various embodiments, the threshold value associated with a certain vital sign parameter may depend on a measured value of one, or more than one vital sign parameters.

Figure 7B:
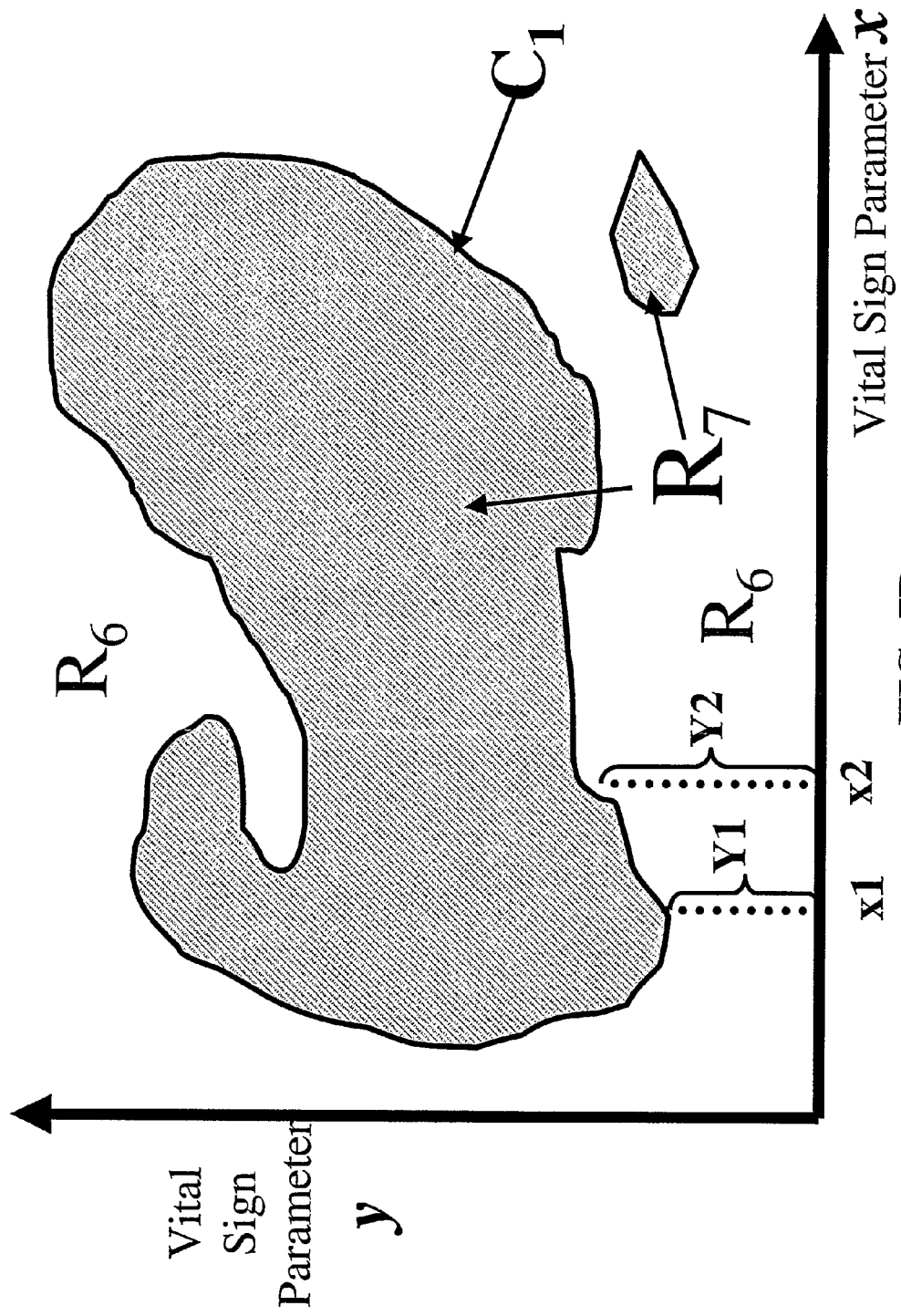
FIG. 7B provides an illustration of partitioning a parameter space in accordance with values indicative of a severity and/or forecasted likelihood of an onset of a potentially life-threatening condition in accordance with some embodiments of the present invention.

FIG. 7A refers to the particular case where each region is contiguous. It is appreciated that this is not a limitation, as illustrated in FIG. 7B, where region $R_7$ is not contiguous.

Apparatus for Generating a Forecast

Figure 8A:
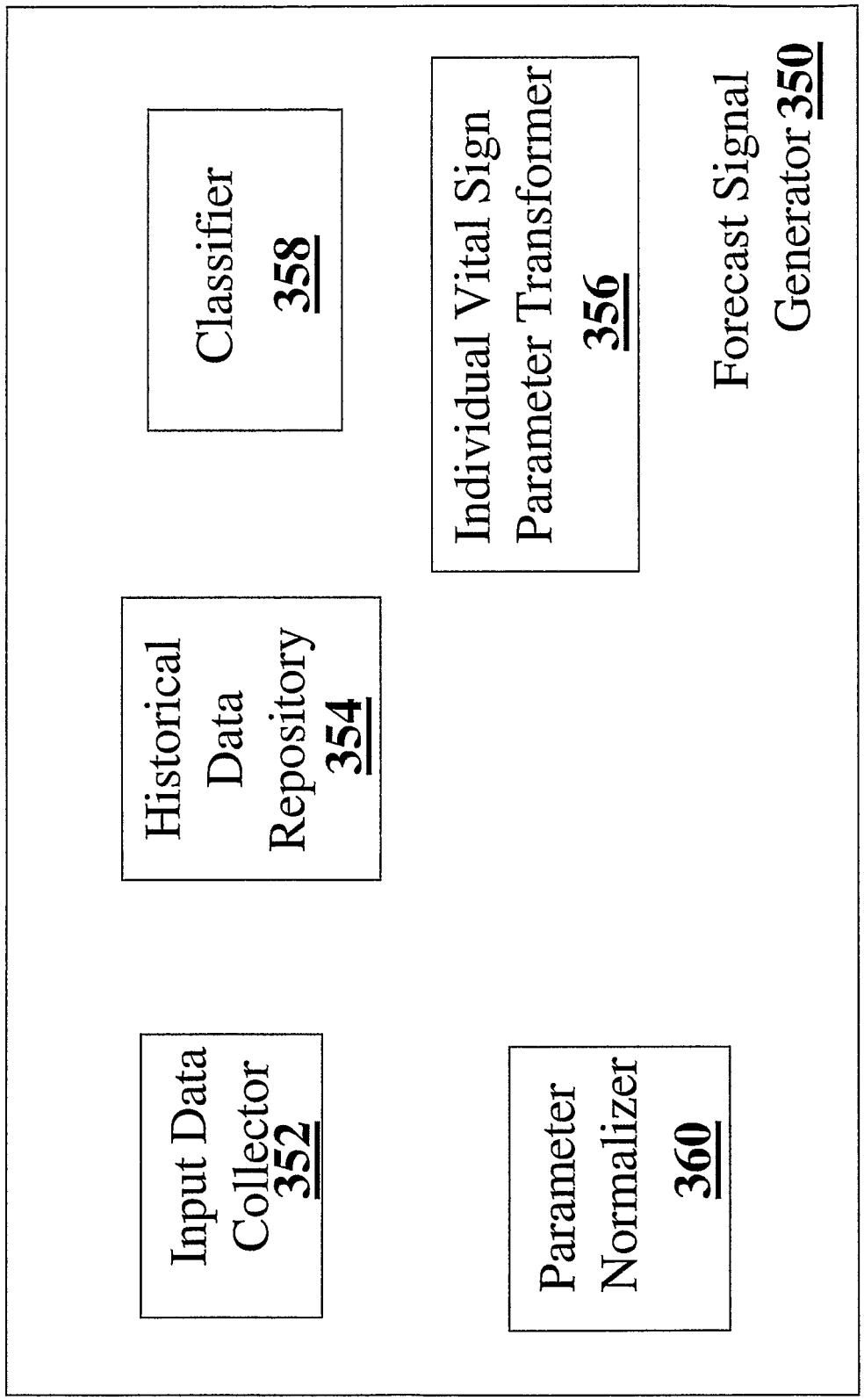
FIG. 8A provides a block diagram of an exemplary forecast generator.
Figure 8B:
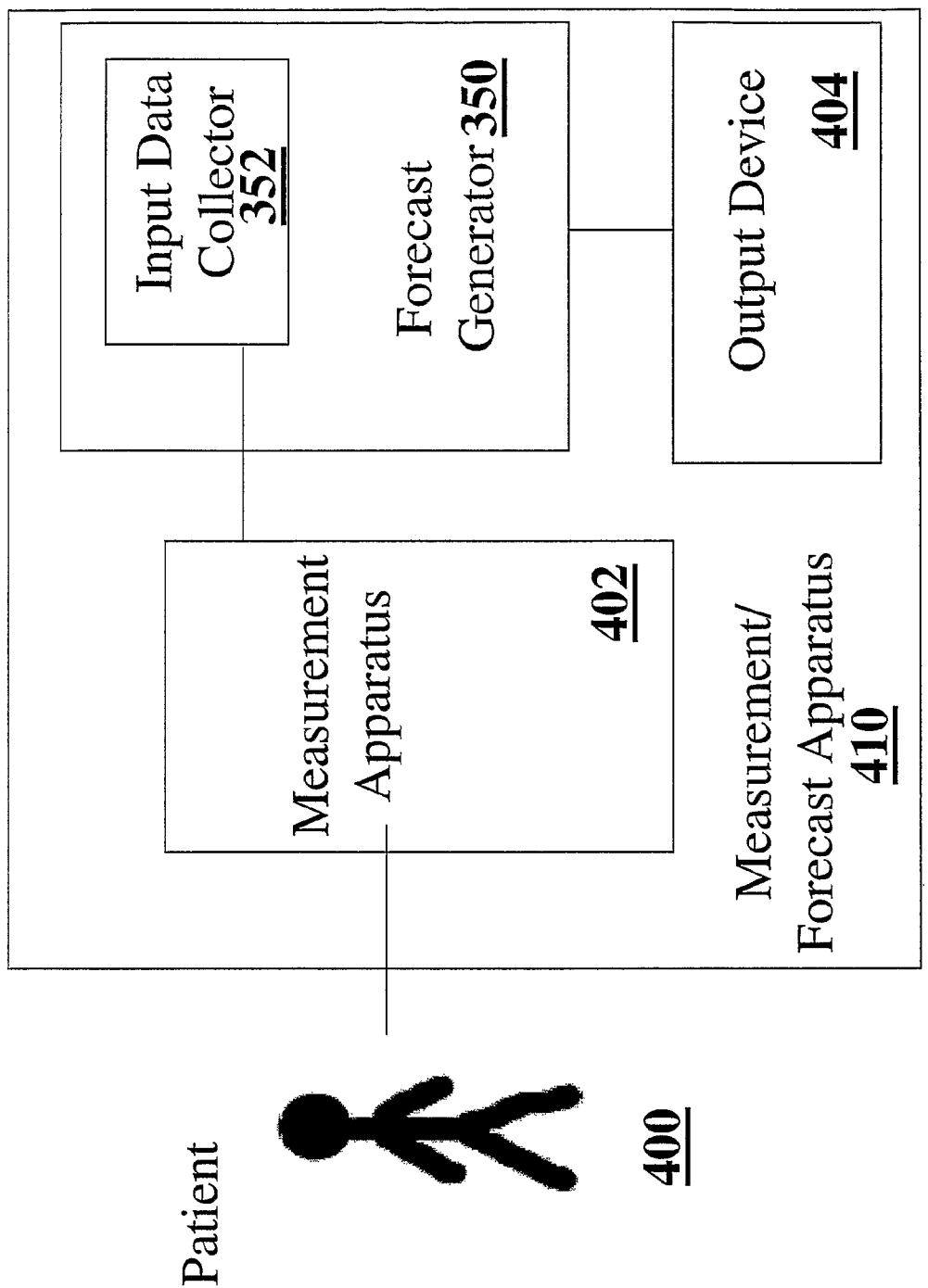
FIG. 8B provides a block diagram of an exemplary apparatus adapted to measure vital sign parameters and to generate a forecast.

FIG. 8A provides a block diagram of exemplary apparatus (i.e. a forecast generator 360) for generating a forecast for the potentially life-threatening condition. The exemplary forecast generator 350 includes an input data collector 352 (for measuring vital sign parameters and/or for receiving measurements from a measurement apparatus 402 as shown in FIG. 8B). A parameter normalizer 360 may optionally be provided, for example for normalizing one or more vital sign parameters (for example, see step 210 above). Furthermore, a vital sign parameter transformer 356 may be provided, for example, for computing, for one or more vital signed parameters, transformed values of the parameters (for example, see step 212 above). As shown in FIG. 8A, the system further includes a classifier 358, for generating, for example, a forecast by "classifying" current values and/or historical values of one or more measurement values of one or more vital sign parameters (and/or transformed values). Historical values 354 of forecasts and/or measurement values may be stored in a historical data repository 354, allowing the system to be a "learning system" which may compare current trends and/or values with historical trends and/or values for a particular patient.

FIG. 8B provides a block diagram of measurement/forecast apparatus 410, for measuring physiological parameters and/or vital signs for a particular patient 400 and for generating a forecast in accordance with values measured by the measurement apparatus 402. The measurement apparatus 402 may include, for example, an EKG, a temperature-measurement device (wired or wireless) or any other device operative to measure a desired vital sign parameter.

It is noted that the presently disclosed apparatus and methods may be implemented using any combination of hardware and software.

The following examples are to be considered merely as illustrative and non-limiting in nature. It will be apparent to one skilled in the art to which the present invention pertains that many modifications, permutations, and variations may be made without departing from the scope of the invention.

Experimental Methods and Results

A device (i.e. computer hardware configured with software) which implements the presently-disclosed techniques for predicting Sepsis was constructed. The "Sepsis Index" (i.e. a number output by the device indicative of a forecast of a likelihood or probability that a particular infant will contract Sepsis) on 24 premature infants in the Intensive Care Unit at the Neonatal Premature department Laniado Medical Center, Natanya, Israel. Mostly were extreme low birth weight premature babies. Three of the Infants had proven sepsis episodes, one of those have had 2 episodes. The Sepsis Index detected all the 4 episodes 18-36 hours in advance. Five premature babies were treated with antibiotics due to a clinical sepsis suspect. In all of them the Sepsis Index was in normal range, the blood cultures were normal and we discontinued the antibiotic therapy. In 18 babies there was no evidence of sepsis either clinical or according to the Sepsis Index. In 2 babies there were questionable evidence of sepsis according to the Sepsis Index, but no evidence in the clinical or laboratory signs. In conclusion, the Sepsis Index was very reliable in 22 cases and questionable in 2

| Nr | Initials | Birth Date | Birth Weight (Gram) | Gest. Age week | Follow up period | Sepsis Index Y/N | Hours In Advance | Sepsis Evidence Y/N | Antibio. Therapy Contin/disco. | Reliability Of index |
|---|---|---|---|---|---|---|---|---|---|---|
| 1. | T. Girl | 29.6.05 | 1540 | 38 | 25.7-25.8.05 | N | | N | | good |
| 2. | Z. Girl | 12.7.05 | 1350 | 31 | 19.7-24.8.05 | N | | N | | good |
| 3. | I. Girl | 14.7.05 | 1060 | 32 | 21.7-24.8.05 | N | | N | Discontinue. | good |
| 4. | P. Boy | 22.7.05 | 1490 | 29 | 22.7-12.9.05 | N | | N | | good |
| 5. | B. Boy | 16.8.05 | 830 | 27 | 17.8-31.8.05 | N | | N | | good |
| 6. | M. Boy | 20.8.05 | 640 | 27 | 20.8-2.10.05 | Y | 24 | Y | Continue | good |
| | | | | | | Y | 36 | Y | Continue | good |
| 7. | A. Boy | 26.8.05 | 1130 | 28 | 26.8-21.10.05 | N | | N | | good |
| 8. | H. Boy | 28.8.05 | 1320 | 30 | 28.8-2.10.05 | N | | N | Discontinue | good |
| 9. | F1. Girl | 1.9.05 | 1380 | 33 | 1.9-21.9.05 | N | | N | | good |
| 10. | F2. Girl | 1.9.05 | 1450 | 33 | 1.9-22.9.05 | N | | N | | good |
| 11. | G. Boy | 9.9.05 | 810 | 25 | 12.9-2.10.05 | N | | N | Discontinue | good |
| 12. | P. Boy | 22.9.05 | 1735 | 31 | 26.9-2.10.05 | N | | N | | good |
| 13. | A. Boy | 26.11.05 | 620 | 23 | 29.11-28.12.05 | Y | 23 | Y | Continue | good |
| 14. | M. Boy | 2.12.05 | 1030 | 27 | 6.12.05-22.1.06 | Y? | | N | | questionable |
| 15. | B. Boy | 6.12.05 | 1150 | 31 | 6.12.05-30.1.06 | N | | N | | good |
| 16. | S. Boy | 9.12.05 | 1120 | 29 | 9.12.05-22.1.06 | N | | N | | good |
| 17. | D. Boy | 17.12.05 | 930 | 26 | 21.12.05-22.1.06 | Y? | | N | | questionable |
| 18. | B. Boy | 28.12.05 | 1230 | 27 | 28.12.05-22.1.05 | N | | N | Discontinue | good |
| 19. | A. Boy | 18.2.06 | 1480 | 28 | 3.3.-2.4.06 | N | | N | Discontinue | good |
| 20. | G. Girl | 23.2.06 | 1070 | 31 | 2.3.-16.4.06 | N | | N | | good |
| 21. | B. Boy | 17.2.06 | 1020 | 28 | 18.2.-16.4.06 | Y | 18 | Y | Continue | good |
| 22. | G. Girl | 17.2.06 | 720 | 28 | 1.3.-15.4.06 | N | | N | | good |
| 23. | G. Boy | 23.3.06 | 1420 | 30 | 24.3-16.4.06 | N | | N | | good |
| 24. | A. Boy | 5.4.06 | 1030 | 34 | 6.4-16.4.06 | N | | N | | good |

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

All references cited herein are incorporated by reference in their entirety. Citation of a reference does not constitute an admission that the reference is prior art.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

What is claimed is:

1. A method of forecasting a condition of sepsis in a premature infant comprising:
    a) using physiological sensors to acquire a plurality of different vital sign parameters of an infant, the physiological sensors connected to one or more processors and providing measurement values to the one or more processors of the plurality of different vital sign parameters of the infant;
    b) the one or more processors normalizing measurement values of the plurality of different vital signs including, for each of the different vital sign parameters of the infant that is not a bradycardia parameter, normalizing the each of the different vital sign parameters against historical values for said infant, the one or more processors transforming said normalized or un-normalized value;
    c) the one or more processors combining the transformed measurement values of the plurality of different vital sign parameters and thereby generating a single sepsis parameter, the single sepsis parameter comprising a single variable having a variable numerical value;
    d) the one or more processors monitoring the single sepsis parameter of the infant over time; and
    e) the one or more processors generating a forecast of the condition of sepsis in the infant from said single sepsis parameter when the single sepsis parameter reaches beyond a normal range.

2. The method of claim 1 wherein providing measurement values of the plurality of different vital sign parameters includes providing measurement values of a heart rate parameter.

3. The method of claim 1 wherein providing measurement values includes providing at least one said vital sign parameter that is a respiratory parameter, the respiratory parameter selected from (i) respiration rate and (ii) a parameter indicative of an apnea condition.

4. The method of claim 1 wherein providing measurement values of the plurality of different vital sign parameters comprises providing measurement values of a temperature parameter, a desaturation parameter, a heart rate parameter, a bradycardia parameter, and a respiration rate parameter.

5. The method of claim 4 wherein providing measurement values includes providing measurement values for a body weight of the infant.

6. The method of claim 1 wherein providing measurement values of the plurality of different vital sign parameters includes providing measurement values of a first vital sign parameter and a second-vital sign parameter, the first and second vital sign parameters being associated with different respective physiological systems of the infant.

7. The method of claim 1 wherein said generating of said forecast includes computing an arithmetic function of a first number derived from a measured value of a first said vital sign parameter and of a second number from a measured value of a second said vital sign parameter that is different from said first vital sign parameter.

8. The method of claim 1 wherein providing measurement values of the plurality of different vital sign parameters includes providing measurement values of at least two of the different vital sign parameters, the at least two of the different vital sign parameters being associated with different respective physiological systems of the infant and wherein one of the different vital sign parameters is a cardiac parameter.

9. The method of claim 1 further comprising:
  f) generating an alarm signal in accordance with said forecast.

10. The method of claim 1 wherein said generating includes generating a forecast for the onset of late-onset infant sepsis.

11. The method of claim 1 wherein said infant is a very low birth weight infant.

12. The method of claim 1 wherein the one or more processors generates the forecast at least in part by a relation between a measured value of a first said vital sign parameter and at least one threshold value associated with said first vital sign, and at least one said threshold value for said first vital sign depends at least in part on a said measured values of a second vital sign different from said first vital sign.

13. The method of claim 12 wherein providing measurement values includes providing that at least one of said first vital sign parameter and said second vital sign parameter is other than a cardiac vital sign parameter.

14. The method of claim 1 wherein providing measurement values includes providing values for at least one said vital sign parameter that are acquired -for a plurality of times, and said forecast is determined at least in part by said values for said plurality of times.

15. The method of claim 1 wherein providing measurement values includes providing at least one said vital sign parameter indicative of a state of the skin.

16. The method of claim 1 further comprising acquiring an age parameter of the infant and providing measurement values to the one or more processors of the age of the infant; and further comprising the one or more processors normalizing the measurement values of at least one of the particular vital sign parameters against the age of the infant.

17. The method of claim 3 wherein providing measurement values includes providing at least one said vital sign parameter that is a respiration rate parameter.

18. The method of claim 1 wherein providing measurement values includes providing at least one said vital sign parameter that is a temperature parameter.

19. The method of claim 1 wherein providing measurement values includes providing at least one said vital sign parameter that is a desaturation parameter.

20. The method of claim 1 wherein providing measurement values includes providing at least one said vital sign parameter that is a metabolic parameter.

21. The method of claim 1 wherein providing measurement values includes providing at least one said vital sign parameter that is indicative of a rate of gas exchange.

22. The method of claim 1 wherein providing measurement values includes providing at least one said vital sign parameter that is indicative of a concentration of a substance in a biological fluid.

23. The method of claim 1 wherein providing measurement values includes providing at least one said vital sign parameter that is indicative of a increase or decrease in tissue mass.

24. The method of claim 1 wherein providing measurement values includes providing at least one said vital sign parameter that is indicative of a cell replication.

25. The method of claim 1 wherein providing measurement values includes providing at least one said vital sign parameter that is a parameter indicative of an apnea condition.

26. The method of claim 1 wherein providing measurement values includes providing at least one said vital sign parameter that is a digestion parameter.

27. The method of claim 1 wherein providing measurement values includes providing at least one said vital sign parameter that is indicative of a —stable relationship between the patient and the external environment.

28. The method of claim 1 wherein providing measurement values includes providing at least one said vital sign parameter that is a cardiac parameter.

29. The method of claim 28 wherein providing measurement values includes providing said vital sign parameter that is selected from the group consisting of a heart rate parameter and a bradycardia parameter.

30. The method of claim 1 further comprising acquiring an age parameter and a body mass parameter of the infant and providing measurement values to the one or more processors of the age and body mass of the infant; and further comprising the one or more processors normalizing the measurement values of at least one of the particular vital sign parameters against the age and body mass of the infant.

31. The method of claim 30, wherein providing one of said normalized vital sign parameters that include a temperature parameter.

32. The method of claim 1 wherein said generating of said forecast includes normalizing more than one of said plurality of said vital sign parameters in accordance with a respective normalization function that is different for each said vital sign parameter of said plurality.

33. The method of claim 1 wherein said generating of said forecasts includes acquiring a temperature parameter and a cardiac parameters and wherein the temperature parameter and the cardiac parameter are normalized using different functions.

34. The method of claim 1 wherein providing measurement values includes providing that for each said vital sign parameter,
  i) said measured values are acquired —for a respective plurality of points in time;
  ii) said forecast is generated in accordance with said measured values for said respective plurality of points in time;
  iii) a ratio between an average time frequency for a first said physiological parameter to an average time frequency for a second sad physiological parameter is at least 2.

35. The method of claim 34 wherein said ratio is at least 5.

36. The method of claim 35 wherein said ratio is at least 10.

37. The method of claim 1 further comprising:
continuing to monitor the single sepsis parameter after the single sepsis parameter reaches into the normal range, and discontinuing a course of treatment.

38. An apparatus for forecasting a condition of sepsis in a premature infant, the apparatus comprising:
- a) a data storage unit for storing measurement values for a plurality of different vital sign parameters of an infant, the data storage unit connected to physiological sensors for acquiring the plurality of different vital sign parameters; and
- b) a data processing unit in communication with the data storage unit to receive the plurality of measurement values, the data processing unit including one or more processors configured to normalize each measurement value, for each of the different vital sign parameters that is not a bradycardia parameter, against historical values for said infant, the one or more processors further configured to transform said normalized or un-normalized value,
  the one or more processors also configured to combine the transformed measurement values of the plurality of different vital sign parameters and thereby generate a single sepsis parameter, the single sepsis parameter comprising a single variable having a variable numerical value, and the data processing unit also configured to monitor the single sepsis parameter of the premature infant over time and generate a forecast of the condition of sepsis in the infant from said single sepsis parameter when the single sepsis parameter reaches beyond a normal range.

39. The apparatus of claim 38, wherein the data storage unit is connected to physiological sensors for acquiring a temperature parameter, a desaturation parameter, a heart rate parameter, a bradycardia parameter, and a respiration rate parameter and a body weight of the infant.

40. The apparatus of claim 38, further comprising the one or more processors configured to normalize more than one vital sign parameter of said plurality of said different vital sign parameters in accordance with a respective normalization function that is different for each said vital sign parameters of said plurality.

41. A non-transitory computer readable medium comprising program instructions, wherein when executed the program instructions are operable to:
- a) access measurement values of a plurality of different vital sign parameters of an infant;
- b) normalize each of the plurality of different vital sign parameters that is not a bradycardia parameter against historical values of the infant and transform said normalized or un-normalized values;
  combine the transformed measurement values of the plurality of different vital sign parameters and thereby generate a single sepsis parameter, the single sepsis parameter comprising a single variable having a variable numerical values; and
- c) generate a forecast of the life-threatening condition of sepsis in the infant from said single sepsis parameter when the single sepsis parameter reaches beyond a normal range.

42. The non-transitory computer readable medium comprising program instructions of claim 41, wherein when executed the program instructions are operable to access measurement values of a temperature parameter, a desaturation parameter, a heart rate parameter, a bradycardia parameter, and a respiration rate parameter and a body weight of the infant.

43. An apparatus for forecasting a condition of sepsis in a premature infant, the apparatus comprising:
- a) a data storage unit for storing measurement values for a plurality of different vital sign parameters of an infant, the data storage unit connected to physiological sensors for acquiring the plurality of different vital sign parameters; and
- b) a data processing unit in communication with the data storage unit to receive the measurement values, the data processing unit including one or more processors configured to normalize each measurement value for each of the different vital sign parameters that is not a bradycardia parameter, against a historical values for said infant, the one or more processors configured to transform or leave untransformed each of said normalized or un-normalized values,
  the one or more processors also configured to combine any said transformed and untransformed normalized values and any said transformed and untransformed un-normalized values, of the plurality of different vital sign parameters and thereby generate a single variable having a variable numerical value, and the data processing unit also configured to monitor the single sepsis parameter of the premature infant over time and generate a forecast of the condition of sepsis in the infant from said single sepsis parameter when the single sepsis parameter reaches beyond a normal range.

* * * * *